(12) United States Patent
Abkevich et al.

(10) Patent No.: US 10,851,425 B2
(45) Date of Patent: *Dec. 1, 2020

(54) METHOD FOR TREATING CANCER

(71) Applicant: MYRIAD GENETICS, INC., Salt Lake City, UT (US)

(72) Inventors: Victor Abkevich, Salt Lake City, UT (US); Alexander Gutin, Salt Lake City, UT (US); Kirsten Timms, Salt Lake City, UT (US); Jerry Lanchbury, Salt Lake City, UT (US)

(73) Assignee: MYRIAD GENETICS, INC., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/576,643

(22) Filed: Sep. 19, 2019

(65) Prior Publication Data

US 2020/0010913 A1    Jan. 9, 2020

Related U.S. Application Data

(63) Continuation of application No. 13/164,499, filed on Jun. 20, 2011, now abandoned.

(60) Provisional application No. 61/356,501, filed on Jun. 18, 2010.

(51) Int. Cl.
*C12Q 1/6886* (2018.01)
*C12Q 1/6827* (2018.01)
*G16B 20/00* (2019.01)

(52) U.S. Cl.
CPC ......... *C12Q 1/6886* (2013.01); *C12Q 1/6827* (2013.01); *G16B 20/00* (2019.02); *C12Q 2527/127* (2013.01); *C12Q 2565/00* (2013.01); *C12Q 2600/106* (2013.01); *C12Q 2600/136* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

2003/0049613 A1    3/2003    Perucho et al.
2010/0145894 A1    6/2010    Semizarov et al.

FOREIGN PATENT DOCUMENTS

WO         2006/128195 A2    11/2006
WO         WO-2011160063 A2 * 12/2011    ............ C12Q 1/6827

OTHER PUBLICATIONS

Nannya et al. (Cancer Res, 2005; 65; pp. 6071-6079) (Year: 2005).*
Leunen K etal (Human Mutation, vol. 30, No. 12, Dec. 2009, pp. 1693-1702) (Year: 2009).*
Extended European Search Report issued in EP15189527.3 dated Mar. 31, 2016 (14 pages).
IFW of U.S. Appl. No. 13/164,499, filed Jun. 20, 2011, Inventors Victor Abkevich et al.
IFW of U.S. Appl. No. 14/554,715, filed Nov. 26, 2014, Inventors Victor Abkevich et al.
Leunen et al., "Recurrent copy number alterations in BRCAI-mutated ovarian tumors alter biological pathways", Human Mutation, vol. 30, No. 12, Dec. 1, 2009 (Dec. 1, 2009), pp. 1693-1702.
Gunnarsson et al., "Large but not small copy-number alterations correlate to high-risk genomic aberrations and survival in chronic lymphocytic leukemia: a high-resolution genomic screening of newly diagnosed patients", Leukemia, vol. 24, No. I, Jan. 1, 2010 (Jan. 1, 2010), pp. 211-215.
Kujawski et al., "Genomic complexity identifies patients with aggressive chronic lymphocytic leukemia", Blood, vol. 112, No. 5, Sep. 1, 2008 (Sep. 1, 2008), pp. 1993-2003.
Gorringe et al., Are there any more ovarian tumor suppressor genes? A new perspective using ultra high-resolution copy number and loss of heterozygosity analysis, Genes Chromosomes & Cancer, John Wiley & Sons, Inc. US, vol. 48, No. 10, Oct. 1, 2009 (Oct. 1, 2009), pp. 931-942.
Pfeifer et al., "Genome-wide analysis of DNA copy number changes and LOH in CLL using high-density SNP arrays", Blood, vol. 109, No. 3, Oct. 5, 2006 (Oct. 5, 2006), pp. 1202-1210.
Janne et al., "High-resolution single-nucleotide polymorphism array and clustering analysis of loss of heterozygosity in human lung cancer cell lines", Oncogene, vol. 23, No. 15, Mar. 29, 2004 (Mar. 29, 2004), pp. 2716-2726.
Choi et al., "Genetic classification of colorectal cancer based on chromosomal loss and microsatellite instability predicts survival", Clinical Cancer Research, The American Association for Cancer Research, US, vol. 8, No. 7, Jul. 1, 2002 (Jul. 1, 2002), pp. 2311-2322.
Beroukhim et al., "Inferring Loss-of-Heterozygosity from Unpaired Tumors Using High-Density Oligonucleotide SNP Arrays", Bioinformatics, vol. 19, No. 5, Jan. 1, 2006 (Jan. 1, 2006) p. 2397.
Nannya et al., "A Robust Algorithm for Copy Number Detection Using High-Density Oligonucleotide Single Nucleotide Polymorphism Genotyping Arrays", Cancer Research, American Association for Cancer Research, US • vol. 65, No. 14 Jul. 14, 2005 (Jul. 14, 2005), pp. 6071-6079.

(Continued)

*Primary Examiner* — Pablo S Whaley
(74) *Attorney, Agent, or Firm* — FisherBroyles, LLP; Jason M. Pass; Victoria L. Boyd

(57) ABSTRACT

This document provides methods and materials involved in assessing samples (e.g., cancer cells) for the presence of a loss of heterozygosity (LOH) signature. For example, methods and materials for determining whether or not a cell (e.g., a cancer cell) contains an LOH signature are provided. Materials and methods for identifying cells (e.g., cancer cells) having a deficiency in homology directed repair (HDR) as well as materials and methods for identifying cancer patients likely to respond to a particular cancer treatment regimen also are provided.

13 Claims, 15 Drawing Sheets

(56) References Cited

OTHER PUBLICATIONS

Goransson et al., "Quantification of Normal Cell Fraction and Copy Number Neutral LOH in Clinical Lung Cancer Samples Using SNP Array Data", PLOS ONE, vol. 4, No. 6, Jun. 26, 2009 (Jun. 26, 2009), p. e6057.

Meadows et al., "Genome-wide analysis of loss of heterozygosity and copy number amplification in uterine leiomyomas using the 1OOK single nucleotide polymorphism array", Experimental and Molecular Pathology, vol. 91, No. I, Apr. 8, 2011 (Apr. 8, 2011), pp. 434-439.

Abkevich et al., "Patterns of genomic loss of heterozygosity predict homologous recombination repair defects in epithelial ovarian cancer", British Journal of Cancer, vol. 107, No. 10, Oct. 9, 2012 (Oct. 9, 2012), pp. 1776-1782.

Kotliarov et al, "Supplemental Material: Table SI: Validation of copy number determinations by Real Time PCR SNP ID Adjacent Gene Sample Copy Number by Real-Time PCR Copy Number by CCNT SNP A",—1712744 CDKN2AHF505 0.10 0.47 HF1382 0.14 0,Oct. 1, 2006 (Oct. 1, 2006), pp. 5-1713144, XP055085899, Retrieved from the Internet: URL:http://cancerres.aacrjournals.org/cont ent/suppl/2006/10/04/66.19.9428.DC2/Supplementary_Tables_1-5.pdf[retrieved on Oct. 29, 2013].

De Waal et al., "Secondary Ovarian Malignancies: Frequency, Origin, and Characteristics", Int J Gynecol Cancer, Oct. 2009;19(7):1160-5. doi: 10.1111/IGC.0b013e3181b33cce.

Li et al., "Single nucleotide polymorphism-based genome-wide chromosome copy change, loss of heterozygosity, and aneuploidy in Barrett's esophagus neoplastic progression", Cancer Prev Res, Nov. 2008;1(6):413-23. doi: 10.1158/1940-6207.CAPR-08-0121.

Affymetric Data Sheet "Gene-Chip Human Mapping 100K Set"; published 2005.

\* cited by examiner

Figure 9

| Status | Number of Samples | Percent |
|---|---|---|
| BRCA Deficient | 44 | 33% |
| HDR Deficient/BRCA Intact | 18 | 13% |
| HDR Intact | 72 | 54% |
| Total | 134 | 100% |

METHOD FOR TREATING CANCER

CROSS-REFERENCE TO RELATED APPLICATIONS

This application is a continuation of U.S. patent application Ser. No. 13/164,499, filed Jun. 20, 2011, which claims priority to U.S. Provisional Application Ser. No. 61/356,501 filed Jun. 18, 2010, the entire contents of each of which are hereby incorporated by reference.

BACKGROUND

1. Technical Field

This document relates to methods and materials involved in assessing samples (e.g., cancer cells) for the presence of a loss of heterozygosity (LOH) signature. For example, this document provides methods and materials for determining whether or not a cell (e.g., a cancer cell) contains an LOH signature. This document also provides materials and methods for identifying cells (e.g., cancer cells) having a deficiency in homology directed repair (HDR) as well as materials and methods for identifying cancer patients likely to respond to a particular cancer treatment regimen.

2. Background Information

Cancer is a serious public health problem, with 562,340 people in the United States of America dying of cancer in 2009 alone. *American Cancer Society, Cancer Facts & Figures* 2009 (available at American Cancer Society website). One of the primary challenges in cancer treatment is discovering relevant, clinically useful characteristics of a patient's own cancer and then, based on these characteristics, administering a treatment plan best suited to the patient's cancer. While strides have been made in this field of personalized medicine, there is still a significant need for better molecular diagnostic tools to characterize patients' cancers.

SUMMARY

This document provides methods and materials involved in assessing samples (e.g. cancer cells) for the presence of a loss of heterozygosity (LOH) signature. For example, this document provides methods and materials for determining whether or not a cell (e.g., cancer cell) contains an LOH signature. An LOH signature as used herein refers to the presence of five or more (e.g., six or more, seven or more, eight or more, nine or more, ten or more, eleven or more, 12 or more, 13 or more, 14 or more, 15 or more, 16 or more, 17 or more, 18 or more, 19 or more, or 20 or more) LOH regions that are longer than about 1.5 megabases (e.g., longer than about 2, 2.5, 3, 4, 5, 6, 7, 8, 9, 10, 11, 12, 13, 14, 15, 16, 17, 18, 19, 20, 25, 30, 35, 40, 45, 50, 75, or 100 megabases (Mb)) and are less than the length of the entire chromosome that contains that LOH region. In general, all the chromosomes of a genome for a sample (e.g., tumor biopsy) can be assessed for the presence of an LOH signature. In some cases, all the chromosomes of a genome for a sample with the exception of chromosome 17 can be assessed for the presence of an LOH signature. For males only autosomal chromosomes can be assessed for the presence of an LOH signature.

As described herein, cancer cells having a genome containing an LOH signature can be identified as being likely to have a deficiency in homology directed repair (HDR). In some cases, cancer cells having a genome containing an LOH signature can be identified as being likely to have a deficient status in one or more genes involved in HDR. For example, cancer cells having a genome containing an LOH signature can be identified as being likely to have a deficient BRCA1 or BRCA2 status, and cells having a genome lacking an LOH signature can be identified as being likely to have an intact BRCA1 or BRCA2 status.

Determining whether a cell (e.g., a cancer cell) is likely to have a deficiency in HDR or is likely to have a deficient status in one or more genes involved in HDR can indicate that the mammal (e.g., human) with that cell is likely to have one or more genetic defects within the mammal's germline. Identifying humans with an increased likelihood of having such a germline defect can allow the human or clinicians to inform offspring of the possible inheritance of such a germline defect. Such offspring can elect, based at least in part on such information, to undergo genetic testing and possible monitoring (e.g., early detection monitoring) for the development of cancer.

As also described herein, cancer cells having a genome containing an LOH signature can be identified as being likely to respond to a particular cancer treatment regimen. For example, patients having cancer cells with a genome containing an LOH signature can be identified as being likely to respond to a cancer treatment regimen that includes the use of a DNA damaging agent, a PARP inhibitor, radiation, or a combination thereof. In some cases, patients having cancer cells with a genome lacking an LOH signature can be identified as being unlikely to respond to a cancer treatment regimen designed to administer a single agent such as a single DNA damaging agent, a single PARP inhibitor, or radiation alone. In some cases, patients having cancer cells with a genome lacking an LOH signature can be identified as being likely to respond to a cancer treatment regimen that includes the use of a standard cancer treatment agent not associated with HDR (e.g., a taxol compound such as paclitaxel).

Determining whether or not cancer patients are likely to respond to a particular cancer treatment regimen as described herein can allow patients and clinicians to proceed with a treatment regimen having an increased likelihood of treating cancer (e.g., reducing the number of cancer cells within a patient). In some cases, determining whether or not cancer patients are likely to respond to a particular cancer treatment regimen as described herein can allow patients and clinicians to select the most effective initial cancer treatment regimen for that patient.

In general, one aspect of this document features a method for assessing LOH in a cancer cell or genomic DNA thereof. The method comprises, or consists essentially of, (a) detecting, in a cancer cell or genomic DNA derived therefrom, LOH regions in at least one pair of human chromosomes of the cancer cell, wherein the at least one pair of human chromosomes is not a human X/Y sex chromosome pair; and (b) determining the total number of LOH regions, in the at least one pair of human chromosomes, that are longer than a first length but shorter than the length of the whole chromosome containing the LOH region, wherein the first length is about 1.5 or more megabases.

In another aspect, this document features a method of predicting the status of BRCA1 and BRCA2 genes in a cancer cell. The method comprises, or consists essentially of, determining, in the cancer cell, the total number of LOH regions in at least one pair of human chromosomes of the cancer cell that are longer than a first length but shorter than the length of the whole chromosome containing the LOH region, wherein the at least one pair of human chromosomes is not a human X/Y sex chromosome pair, wherein the first length is about 1.5 or more megabases; and correlating the total number that is greater than a reference number with an increased likelihood of a deficiency in the BRCA1 or BRCA2 gene.

In another aspect, this document features a method of predicting the status of HDR in a cancer cell. The method comprises, or consists essentially of, determining, in the cancer cell, the total number of LOH regions in at least one pair of human chromosomes of the cancer cell that are longer than a first length but shorter than the length of the whole chromosome containing the LOH region, wherein the at least one pair of human chromosomes is not a human X/Y sex chromosome pair, wherein the first length is about 1.5 or more megabases; and correlating the total number that is greater than a reference number with an increased likelihood of a deficiency in HDR.

In another aspect, this document features a method of predicting a cancer patient's response to a cancer treatment regimen comprising a DNA damaging agent, an anthracycline, a topoisomerase I inhibitor, radiation, and/or a PARP inhibitor. The method comprises, or consists essentially of, determining, in a cancer cell from the cancer patient, the number of LOH regions in at least one pair of human chromosomes of a cancer cell of the cancer patient that are longer than a first length but shorter than the length of the whole chromosome containing the LOH region, wherein the at least one pair of human chromosomes is not a human X/Y sex chromosome pair, wherein the first length is about 1.5 or more megabases; and correlating the total number that is greater than a reference number with an increased likelihood that the cancer patient will respond to the cancer treatment regimen.

In another aspect, this document features a method of predicting a cancer patient's response to a treatment regimen. The method comprises, or consists essentially of, determining, in a cancer cell from the cancer patient, the total number of LOH regions in at least one pair of human chromosomes of a cancer cell of the cancer patient that are longer than a first length but shorter than the length of the whole chromosome containing the LOH region, wherein the at least one pair of human chromosomes is not a human X/Y sex chromosome pair, wherein the first length is about 1.5 or more megabases; and correlating the total number that is greater than a reference number with an increased likelihood that the cancer patient will not respond to a treatment regimen including paclitaxel or docetaxel.

In another aspect, this document features a method of treating cancer. The method comprises, or consists essentially of, (a) determining, in a cancer cell from a cancer patient or genomic DNA obtained therefrom, the total number of LOH regions in at least one pair of human chromosomes of the cancer cell that are longer than a first length but shorter than the length of the whole chromosome containing the LOH region, wherein the at least one pair of human chromosomes is not a human X/Y sex chromosome pair, wherein the first length is about 1.5 or more megabases; and (b) administering to the cancer patient a cancer treatment regimen comprising one or more drugs chosen from the group consisting of DNA damaging agents, anthracyclines, topoisomerase I inhibitors, and PARP inhibitors, if the total number of LOH regions is greater than a reference number.

For any one or more of the methods described in the preceding six paragraphs, any one or more of the following can be applied as appropriate. The LOH regions can be determined in at least two, five, ten, or 21 pairs of human chromosomes. The cancer cell can be an ovarian, breast, or esophageal cancer cell. The total number of LOH regions can be 9, 15, 20 or more. The first length can be about 6, 12, or 15 or more megabases. The reference number can be 6, 7, 8, 9, 10, 11, 12, 13, or greater. The at least one pair of human chromosomes can exclude human chromosome 17. The DNA damaging agent can be cisplatin, carboplatin, oxalaplatin, or picoplatin, the anthracycline can be epirubincin or doxorubicin, the topoisomerase I inhibitor can be campothecin, topotecan, or irinotecan, or the PARP inhibitor can be iniparib, olaparib or velapirib.

In another aspect, this document features the use of one or more drugs selected from the group consisting of DNA damaging agents, anthracyclines, topoisomerase I inhibitors, and PARP inhibitors, in the manufacture of a medicament useful for treating a cancer in a patient identified as having a cancer cell determined to have a total of 5 or more Indicator LOH Regions. The Indicator LOH Regions can be determined in at least two, five, ten, or 21 pairs of human chromosomes. The cancer cell can be an ovarian, breast, or esophageal cancer cell. The total number of Indicator LOH Regions can be 9, 15, 20 or more. The Indicator LOH Regions can have a length of about 6, 12, or 15 or more megabases. The Indicator LOH Regions can be present on a chromosome other than human chromosome 17. The DNA damaging agent can be a platinum-based chemotherapy drug, the anthracycline can be epirubincin or doxorubicin, the topoisomerase I inhibitor can be campothecin, topotecan, or irinotecan, or the PARP inhibitor can be iniparib, olaparib or velapirib.

In another aspect, this document features the use of a plurality of oligonucleotides capable of hybridizing to a plurality of polymorphic regions of human genomic DNA, in the manufacture of a diagnostic kit useful for determining the total number of Indicator LOH Regions in at least a chromosome pair of a human cancer cell obtained from a cancer patient, and for detecting (a) an increased likelihood of a deficiency in the BRCA1 or BRCA2 gene in the cancer cell, (b) an increased likelihood of a deficiency in HDR in the cancer cell, or (c) an increased likelihood that the cancer patient will respond to cancer treatment regimen comprising a DNA damaging agent, an anthracycline, a topoisomerase I inhibitor, radiation, or a PARP inhibitor. The Indicator LOH Regions can be determined in at least two, five, ten, or 21 pairs of human chromosomes. The cancer cell can be an ovarian, breast, or esophageal cancer cell. The total number of Indicator LOH Regions can be 9, 15, 20 or more. The Indicator LOH Regions can have a length of about 6, 12, or 15 or more megabases. The Indicator LOH Regions can be present on a chromosome other than human chromosome 17.

In another aspect, this document features a system for determining LOH status of a cancer cell of a cancer patient. The system comprises, or consists essentially of, (a) a sample analyzer configured to produce a plurality of signals about genomic DNA of at least one pair of human chromosomes of the cancer cell, and (b) a computer sub-system programmed to calculate, based on the plurality of signals, the number of Indicator LOH Regions in the at least one pair of human chromosomes. The computer sub-system can be programmed to compare the number of Indicator LOH Regions to a reference number to determine (a) a likelihood of a deficiency in BRCA1 and/or BRCA2 genes in the cancer cell, (b) a likelihood of a deficiency in HDR in the cancer cell, or (c) a likelihood that the cancer patient will respond to cancer treatment regimen comprising a DNA damaging agent, an anthracycline, a topoisomerase I inhibitor, radiation, or a PARP inhibitor. The system can comprise an output module configured to display the likelihood of (a), (b), or (c). The system can comprise an output module configured to display a recommendation for the use of the cancer treatment regimen. The Indicator LOH Regions can be determined in at least two, five, ten, or 21 pairs of human chromosomes. The cancer cell can be an ovarian, breast, or esophageal cancer cell. The total number of Indicator LOH Regions can be 9, 15, 20, or more. The Indicator LOH Regions can have a length of about 6, 12, or 15 or more megabases. The Indicator LOH Regions can be present on chromosomes other than a human chromosome 17. The DNA damaging agent can be a platinum-based chemotherapy drug, the anthracycline can be epirubincin or doxorubicin, the topoisomerase I inhibitor can be campothecin, topotecan, or irinotecan, or the PARP inhibitor can be iniparib, olaparib or velapirib.

In another aspect, this document features a computer program product embodied in a computer readable medium that, when executing on a computer, provides instructions for detecting the presence or absence of any LOH region along one or more of human chromosomes other than the human X and Y sex chromosomes, and the LOH region having a length of about 1.5 or more megabases but shorter than the length of the whole chromosome containing the LOH region; and determining the total number of the LOH region in the one or more chromosome pairs. The computer program product can include other instructions. The Indicator LOH Regions can be determined in at least two, five, ten or 21 pairs of human chromosomes. The cancer cell can be an ovarian, breast, or esophageal cancer cell. The total number of Indicator LOH Regions can be 9, 15, 20, or more. The Indicator LOH Regions can have a length of about 6, 12, or 15 or more megabases. The Indicator LOH Regions can be present on chromosomes other than a human chromosome 17. The DNA damaging agent can be a platinum-based chemotherapy drug, the anthracycline can be epirubincin or doxorubicin, the topoisomerase I inhibitor can be campothecin, topotecan, or irinotecan, or the PARP inhibitor can be iniparib, olaparib or velapirib.

In another aspect, this document features a diagnostic kit. The kit comprises, or consists essentially of, at least 500 oligonucleotides capable of hybridizing to a plurality of polymorphic regions of human genomic DNA; and a computer program product provided herein. The computer program product can be embodied in a computer readable medium that, when executing on a computer, provides instructions for detecting the presence or absence of any LOH region along one or more of human chromosomes other than the human X and Y sex chromosomes, and the LOH region having a length of about 1.5 or more megabases but shorter than the length of the whole chromosome containing the LOH region; and determining the total number of the LOH region in the one or more chromosome pairs. The computer program product can include other instructions. In another aspect, this document features a method for assessing cancer cells of a patient for the presence of an LOH signature. The method comprises, or consists essentially of, (a) detecting the presence of more than a reference number of LOH regions in at least one pair of human chromosomes of a cancer cell of the cancer patient that are longer than a first length but shorter than the length of the whole chromosome containing the LOH region, wherein the at least one pair of human chromosomes is not a human X/Y sex chromosome pair, wherein the first length is about 1.5 or more megabases, and (b) identifying the patient as having cancer cells with the LOH signature.

In another aspect, this document features a method for assessing cancer cells of a patient for the presence of an HDR deficient status. The method comprises, or consists essentially of, (a) detecting the presence of more than a reference number of LOH regions in at least one pair of human chromosomes of a cancer cell of the cancer patient that are longer than a first length but shorter than the length of the whole chromosome containing the LOH region, wherein the at least one pair of human chromosomes is not a human X/Y sex chromosome pair, wherein the first length is about 1.5 or more megabases, and (b) identifying the patient as having cancer cells with the HDR deficient status.

In another aspect, this document features a method for assessing cancer cells of a patient for the presence of a genetic mutation within a gene from an HDR pathway. The method comprises, or consists essentially of, (a) detecting the presence of more than a reference number of LOH regions in at least one pair of human chromosomes of a cancer cell of the cancer patient that are longer than a first length but shorter than the length of the whole chromosome containing the LOH region, wherein the at least one pair of human chromosomes is not a human X/Y sex chromosome pair, wherein the first length is about 1.5 or more megabases, and (b) identifying the patient as having cancer cells with the genetic mutation.

In another aspect, this document features a method for determining if a patient is likely to respond to a cancer treatment regimen comprising administering radiation or a drug selected from the group consisting of DNA damaging agents, anthracyclines, topoisomerase I inhibitors, and PARP inhibitors. The method comprises, or consists essentially of, (a) detecting the presence of more than a reference number of LOH regions in at least one pair of human chromosomes of a cancer cell of the cancer patient that are longer than a first length but shorter than the length of the whole chromosome containing the LOH region, wherein the at least one pair of human chromosomes is not a human X/Y sex chromosome pair, wherein the first length is about 1.5 or more megabases, and (b) identifying the patient as being likely to respond to the cancer treatment regimen.

In another aspect, this document features a method for assessing a patient. The method comprises, or consists essentially of, (a) determining that the patient comprises cancer cells having an LOH signature, wherein the presence of more than a reference number of LOH regions in at least one pair of human chromosomes of a cancer cell of the cancer patient that are longer than a first length but shorter than the length of the whole chromosome containing the LOH region indicates that the cancer cells have the LOH signature, wherein the at least one pair of human chromosomes is not a human X/Y sex chromosome pair, wherein the first length is about 1.5 or more megabases, and (b) diagnosing the patient as having cancer cells with the LOH signature.

In another aspect, this document features a method for assessing a patient. The method comprises, or consists essentially of, (a) determining that the patient comprises cancer cells having an HDR deficiency status, wherein the presence of more than a reference number of LOH regions in at least one pair of human chromosomes of a cancer cell of the cancer patient that are longer than a first length but shorter than the length of the whole chromosome containing the LOH region indicates that the cancer cells have the HDR deficiency status, wherein the at least one pair of human chromosomes is not a human X/Y sex chromosome pair, wherein the first length is about 1.5 or more megabases, and (b) diagnosing the patient as having cancer cells with the HDR deficient status.

In another aspect, this document features a method for assessing a patient. The method comprises, or consists essentially of, (a) determining that the patient comprises cancer cells having a genetic mutation within a gene from an HDR pathway, wherein the presence of more than a reference number of LOH regions in at least one pair of human chromosomes of a cancer cell of the cancer patient that are longer than a first length but shorter than the length of the whole chromosome containing the LOH region indicates that the cancer cells have the genetic mutation, wherein the at least one pair of human chromosomes is not a human X/Y sex chromosome pair, wherein the first length is about 1.5 or more megabases, and (b) diagnosing the patient as having cancer cells with the genetic mutation.

In another aspect, this document features a method for assessing a patient for a likelihood to respond to a cancer treatment regimen comprising administering radiation or a drug selected from the group consisting of DNA damaging agents, anthracyclines, topoisomerase I inhibitors, and PARP inhibitors. The method comprises, or consists essentially of, (a) determining that the patient comprises cancer cells having an LOH signature, wherein the presence of more than a reference number of LOH regions in at least one pair of human chromosomes of a cancer cell of the cancer patient that are longer than a first length but shorter than the length of the whole chromosome containing the LOH region indicates that the cancer cells have the LOH signature, wherein the at least one pair of human chromosomes is not a human X/Y sex chromosome pair, wherein the first length is about 1.5 or more megabases, and (b) diagnosing, based at least in part on the presence of the LOH signature, the patient as being likely to respond to the cancer treatment regimen.

In another aspect, this document features a method for performing a diagnostic analysis of a cancer cell of a patient. The method comprises, or consists essentially of, (a) detecting the presence of more than a reference number of LOH regions in at least one pair of human chromosomes of the cancer cell that are longer than a first length but shorter than the length of the whole chromosome containing the LOH region, wherein the at least one pair of human chromosomes is not a human X/Y sex chromosome pair, wherein the first length is about 1.5 or more megabases, and (b) identifying the patient as having cancer cells with an LOH signature.

In another aspect, this document features a method for performing a diagnostic analysis of a cancer cell of a patient. The method comprises, or consists essentially of, (a) detecting the presence of more than a reference number of LOH regions in at least one pair of human chromosomes of the cancer cell that are longer than a first length but shorter than the length of the whole chromosome containing the LOH region, wherein the at least one pair of human chromosomes is not a human X/Y sex chromosome pair, wherein the first length is about 1.5 or more megabases, and (b) identifying the patient as having cancer cells with a HDR deficient status.

In another aspect, this document features a method for performing a diagnostic analysis of a cancer cell of a patient. The method comprises, or consists essentially of, (a) detecting the presence of more than a reference number of LOH regions in at least one pair of human chromosomes of the cancer cell that are longer than a first length but shorter than the length of the whole chromosome containing the LOH region, wherein the at least one pair of human chromosomes is not a human X/Y sex chromosome pair, wherein the first length is about 1.5 or more megabases, and (b) identifying the patient as having cancer cells with a genetic mutation within a gene from an HDR pathway.

In another aspect, this document features a method for performing a diagnostic analysis of a cancer cell of a patient to determine if the cancer patient is likely to respond to a cancer treatment regimen comprising administering radiation or a drug selected from the group consisting of DNA damaging agents, anthracyclines, topoisomerase I inhibitors, and PARP inhibitors. The method comprises, or consists essentially of, (a) detecting the presence of more than a reference number of LOH regions in at least one pair of human chromosomes of the cancer cell that are longer than a first length but shorter than the length of the whole chromosome containing the LOH region, wherein the at least one pair of human chromosomes is not a human X/Y sex chromosome pair, wherein the first length is about 1.5 or more megabases, and (b) identifying the patient as being likely to respond to the cancer treatment regimen.

In another aspect, this document features a method for diagnosing a patient as having cancer cells having an LOH signature. The method comprises, or consists essentially of, (a) determining that the patient comprises cancer cells having the LOH signature, wherein the presence of more than a reference number of LOH regions in at least one pair of human chromosomes of a cancer cell of the cancer patient that are longer than a first length but shorter than the length of the whole chromosome containing the LOH region indicates that the cancer cells have the LOH signature, wherein the at least one pair of human chromosomes is not a human X/Y sex chromosome pair, wherein the first length is about 1.5 or more megabases, and (b) diagnosing the patient as having cancer cells with the LOH signature.

In another aspect, this document features a method for diagnosing a patient as having cancer cells with an HDR deficient status. The method comprises, or consists essentially of, (a) determining that the patient comprises cancer cells having the HDR deficiency status, wherein the presence of more than a reference number of LOH regions in at least one pair of human chromosomes of a cancer cell of the cancer patient that are longer than a first length but shorter than the length of the whole chromosome containing the LOH region indicates that the cancer cells have the HDR deficiency status, wherein the at least one pair of human chromosomes is not a human X/Y sex chromosome pair, wherein the first length is about 1.5 or more megabases, and (b) diagnosing the patient as having cancer cells with the HDR deficient status.

In another aspect, this document features a method for diagnosing a patient as having cancer cells with a genetic mutation within a gene from an HDR pathway. The method comprises, or consists essentially of, (a) determining that the patient comprises cancer cells having the genetic mutation, wherein the presence of more than a reference number of LOH regions in at least one pair of human chromosomes of a cancer cell of the cancer patient that are longer than a first length but shorter than the length of the whole chromosome containing the LOH region indicates that the cancer cells have the genetic mutation, wherein the at least one pair of human chromosomes is not a human X/Y sex chromosome pair, wherein the first length is about 1.5 or more megabases, and (b) diagnosing the patient as having cancer cells with the genetic mutation.

In another aspect, this document features a method for diagnosing a patient as being a candidate for a cancer treatment regimen comprising administering radiation or a drug selected from the group consisting of DNA damaging agents, anthracyclines, topoisomerase I inhibitors, and PARP inhibitors. The method comprises, or consists essentially of, (a) determining that the patient comprises cancer cells having an LOH signature, wherein the presence of more than a reference number of LOH regions in at least one pair of human chromosomes of a cancer cell of the cancer patient that are longer than a first length but shorter than the length of the whole chromosome containing the LOH region indicates that the cancer cells have the LOH signature, wherein the at least one pair of human chromosomes is not a human X/Y sex chromosome pair, wherein the first length is about 1.5 or more megabases, and (b) diagnosing, based at least in part on the presence of the LOH signature, the patient as being likely to respond to the cancer treatment regimen.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 9 is a table showing the percent of ovarian cancer samples that are BRCA deficient, HDR deficient/BRCA intact, and HDR intact.

DETAILED DESCRIPTION

Figure 1:
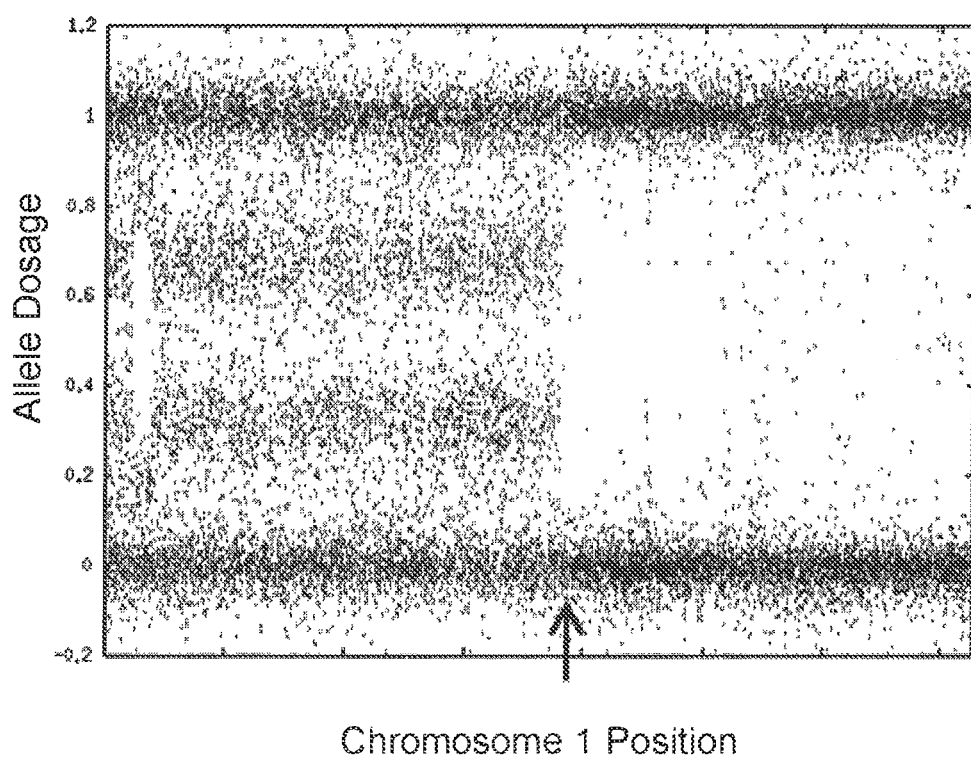
FIG. 1 is a graph plotting allele dosages of breast cancer cells from a breast cancer patient along chromosome 1 as determined using a SNP array. The arrow indicates a transition between a region of heterozygosity and an LOH region.

This document provides methods and materials involved in assessing samples (e.g., cancer cells) for the presence of an LOH signature. For example, this document provides methods and materials for determining whether or not a cell (e.g., a cancer cell) contains an LOH signature.

In general, a comparison of sequences present at the same locus on each chromosome (each autosomal chromosome for males) can reveal whether that particular locus is homozygous or heterozygous within the genome of a cell. Polymorphic loci within the human genome are generally heterozygous within an individual since that individual typically receives one copy from the biological father and one copy from the biological mother. In some cases, a polymorphic locus or a string of polymorphic loci within an individual are homozygous as a result in inheriting identical copies from both biological parents.

Loss of heterozygosity (LOH) may result from several mechanisms. For example, in some cases, a region of one chromosome can be deleted in a somatic cell. The region that remains present on the other chromosome (the other non-sex chromosome for males) is an LOH region as there is only one copy (instead of two copies) of that region present within the genome of the affected cells. This LOH region can be any length (e.g., from a length less than about 1.5 Mb up to a length equal to the entire length of the chromosome). This type of LOH event results in a copy number reduction. In other cases, a region of one chromosome (one non-sex chromosome for males) in a somatic cell can be replaced with a copy of that region from the other chromosome, thereby eliminating any heterozygosity that may have been present within the replaced region. In such cases, the region that remains present on each chromosome is an LOH region and can be referred to as a copy neutral LOH region. Copy neutral LOH regions can be any length (e.g., from a length less than about 1.5 Mb up to a length equal to the entire length of the chromosome).

As described herein, a cellular sample (e.g., cancer cell sample) can be identified as having a positive LOH signature status if the genome of the cells being assessed contains five or more (e.g., six or more, seven or more, eight or more, nine or more, ten or more, eleven or more, 12 or more, 13 or more, 14 or more, 15 or more, 16 or more, 17 or more, 18 or more, 19 or more, or 20 or more) LOH regions that are (a) longer than about 1.5 megabases (e.g., longer than about 2, 2.5, 3, 4, 5, 6, 7, 8, 9, 10, 11, 12, 13, 14, 15, 16, 17, 18, 19, 20, 25, 30, 35, 40, 45, 50, 75, or 100 megabases (Mb)) and (b) less than the length of the entire chromosome that contains that LOH region. In some cases, a cancer cell sample can be identified as having a positive LOH signature status if the genome of the cells being assessed contains nine or more LOH regions that are (a) longer than about 15 Mb and (b) less than the length of the entire chromosome that contains that LOH region. Unless otherwise defined, the term "Indicator LOH Region" refers to an LOH region that is in a pair of human chromosomes other than the human X/Y sex chromosome pair, and that is characterized by loss of heterozygosity with a length of about 1.5 or more megabases but shorter than the length of the whole chromosome containing the LOH region. The length of the whole chromosome containing an LOH region may be determined by examining the length of the shorter chromosome of the corresponding chromosome pair in a germline cell or a non-tumor somatic cell. In some embodiments, an Indicator LOH Region is any LOH region about 2, 2.5, 3, 4, 5, 6, 7, 8, 9, 10, 11, 12, 13, 14, 15, 16, 17, 18, 19, 20, 25, 30, 35, 40, 45, 50, 75, or 100 megabases (Mb)) or more and less than the length of the whole chromosome that contains that LOH region.

Cells (e.g., cancer cells) identified as having a positive LOH signature status can be classified as having an increased likelihood of having an HDR deficiency and/or as having an increased likelihood of having a deficient status in one or more genes in the HDR pathway. For example, cancer cells identified as having a positive LOH signature status can be classified as having an increased likelihood of having an HDR deficient status. In some cases, cancer cells identified as having a positive LOH signature status can be classified as having an increased likelihood of having a deficient status for one or more genes in the HDR pathway. As used herein, deficient status for a gene means the sequence, structure, expression and/or activity of the gene or its product is/are deficient as compared to normal. Examples include, but are not limited to, low or no mRNA or protein expression, deleterious mutations, hypermethylation, attenuated activity (e.g., enzymatic activity, ability to bind to another biomolecule), etc. As used herein, deficient status for a pathway (e.g., HDR pathway) means at least one gene in that pathway (e.g., BRCA1) has a deficient status. Examples of highly deleterious mutations include frameshift mutations, stop codon mutations, and mutations that lead to altered RNA splicing. Deficient status in a gene in the HDR pathway may result in deficiency or reduced activity in homology directed repair in the cancer cells. Examples of genes in the HDR pathway include, without limitation, the genes listed in Table 1.

TABLE 1

Selected HDR Pathway Genes

| Gene Name | Entrez Gene Symbol (if different) | Entrez Gene Id |
|---|---|---|
| BLM | BLM | 641 |
| BRCA1 | BRCA1 | 672 |
| BRCA2 | BRCA2 | 675 |
| CtIP | RBBP8 | 5932 |
| DNA polymerase delta | POLD1 | 5424 |
|  | POLD2 | 5424 |
|  | POLD3 | 10714 |
|  | POLD4 | 57804 |
| DNA polymerase eta | POLH | 5429 |
| DNA2 | DNA2 | 1763 |
| EME1 | EME1 | 146956 |
| ERCC1 | ERCC1 | 2067 |
| EXO1 | EXO1 | 9156 |
| FANCM | FANCM | 57697 |
| GEN1 | GEN1 | 348654 |
| MRE11 | MRE11A | 4361 |
| MUS81 | MUS81 | 80198 |
| NBS1 | NBN | 4683 |
| PAEB2 | PALB2 | 79728 |
| PCNA | PCNA | 5111 |
| RAD50 | RAD50 | 10111 |
| RAD51 | RAD51 | 5888 |
| RAD51AP1 | RAD51AP1 | 10635 |
| RAD51B | RAD51L1 | 5890 |
| RAD51C | RAD51C | 5889 |
| RAD51D | RAD51L3 | 5892 |
| RAD54 | ATRX | 546 |
| RAD54B | RAD54B | 25788 |
| RMI1 | RMI1 | 80010 |
| RMI2 | C16orf75 | 116028 |
| RPA | RPA1 | 6117 |
| RTEL1 | RTEL1 | 51750 |
| SLX1 |  |  |
| SLX2 |  |  |
| SLX4 | SLX4 | 84464 |
| TOP2A | TOP2A | 7153 |
| XPF | ERCC4 | 2072 |
| XRCC2 | XRCC2 | 7516 |
| XRCC3 | XRCC3 | 7517 |

Examples of genetic mutations that can be present within a gene of the HDR pathway include, without limitation, those listed in Table 2.

TABLE 2

Possible genetic mutations within selected genes of the HDR pathway.

| Gene | Mutation | Entrez Gene ID |
|---|---|---|
| BRCA1 | C24F | 672 |
| BRCA1 | E29X | 672 |
| BRCA2 | R3052W | 675 |
| BRCA2 | 2881delG | 675 |
| RAD51C | G125V | 5889 |
| RAD51C | L138F | 5889 |
| RAD51C | Y75XfsX0 | 5889 |

In some cases, a cellular sample (e.g., cancer cell sample) can be identified as having an increased number of LOH regions (e.g., at least 7, 8, 10, or more LOH regions) that cover the whole chromosome. Cells (e.g., cancer cells) identified as having an increased number of LOH regions that cover the whole chromosome can be classified as having an increased likelihood of having intact genes in the HDR pathway. For example, cancer cells identified as having an increased number of LOH regions that cover the whole chromosome can be classified as being more likely to have intact BRCA1 and BRCA2 genes.

As described herein, identifying LOH loci (as well as the size and number of LOH regions) can include, first, determining the genotype of a sample at various genomic loci (e.g., SNP loci, individual bases in large sequencing) and, second, determining whether homozygous loci are due to LOH events. Any appropriate technique can be used to determine genotypes at loci of interest within the genome of a cell. For example, single nucleotide polymorphisms (SNP) arrays (e.g., human genome-wide SNP arrays), targeted sequencing of loci of interest (e.g., sequencing SNP loci and their surrounding sequences), and even untargeted sequencing (e.g., whole exome, transcriptome, or genome sequencing) can be used to identify loci as being homozygous or heterozygous. In some cases, an analysis of the homozygous or heterozygous nature of loci over a length of a chromosome can be performed to determine the length of regions of homozygosity or heterozygosity. For example, a stretch of SNP locations that are spaced apart (e.g., spaced about 25 kb to about 100 kb apart) along a chromosome can be evaluated using SNP array results to determine not only the presence of a region of homozygosity along a chromosome but also the length of that region. Results from a SNP array can be used to generate a graph that plots allele dosages along a chromosome. Allele dosage $d_i$ for SNP i can be calculated from adjusted signal intensities of two alleles ($A_i$ and $B_i$): $d_i=A_i/(A_i+B_i)$. An example of such a graph is presented in FIG. 1.

Once a sample's genotype has been determined for a plurality of loci (e.g., SNPs), common techniques can be used to identify loci and regions of LOH. One way to determine whether homozygosity is due to LOH is to compare the somatic genotype to the germline. For example, the genotype for a plurality of loci (e.g., SNPs) can be determined in both a germline (e.g., blood) sample and a somatic (e.g., tumor) sample. The genotypes for each sample can be compared (typically computationally) to determine where the genome of the germline cell was heterozygous and the genome of the somatic cell is homozygous. Such loci are LOH loci and regions of such loci are LOH regions.

Computational techniques can also be used to determine whether homozygosity is due to LOH. Such techniques are particularly useful when a germline sample is not available for analysis and comparison. For example, algorithms such as those described elsewhere can be used to detect LOH regions using information from SNP arrays (Nannya et al., CANCER RES. (2005) 65:6071-6079). Typically these algorithms do not explicitly take into account contamination of tumor samples with benign tissue. Cf. International Application No. PCT/US2011/026098 to Abkevish et al.; Goransson et al., PLoS ONE (2009) 4(6):e6057. This contamination is often high enough to make the detection of LOH regions challenging. Improved analytical methods according to the present invention for identifying LOH, even in spite of contamination, include those embodied in computer software products as described below.

The following is one example. If the observed ratio of the signals of two alleles, A and B, is two to one, there are two possibilities. The first possibility is that cancer cells have LOH with deletion of allele B in a sample with 50% contamination with normal cells. The second possibility is that there is no LOH but allele A is duplicated in a sample with no contamination with normal cells. An algorithm can be implemented as a computer program as described herein to reconstruct LOH regions based on genotype (e.g., SNP genotype) data. One point of the algorithm is to first reconstruct allele specific copy numbers (ASCN) at each locus (e.g., SNP). ASCNs are the numbers of copies of both paternal and maternal alleles. An LOH region is then determined as a stretch of SNPs with one of the ASCNs (paternal or maternal) being zero. The algorithm can be based on maximizing a likelihood function and can be conceptually akin to a previously described algorithm designed to reconstruct total copy number (rather than ASCN) at each locus (e.g., SNP). See International Application No. PCT/US2011/026098 to Abkevish et al. The likelihood function can be maximized over ASCN of all loci, level of contamination with benign tissue, total copy number averaged over the whole genome, and sample specific noise level. The input data for the algorithm can include or consist of (1) sample-specific normalized signal intensities for both allele of each locus and (2) assay-specific (specific for different SNP arrays and for sequence based approach) set of parameters defined based on analysis of large number of samples with known ASCN profiles.

In some cases, nucleic acid sequencing techniques can be used to identify loci as being homozygous or heterozygous. For example, genomic DNA from a cell sample (e.g., a cancer cell sample) can be extracted and fragmented. Any appropriate method can be used to extract and fragment genomic nucleic acid including, without limitation, commercial kits such as QIAamp DNA Mini Kit (Qiagen), MagNA Pure DNA Isolation Kit (Roche Applied Science) and GenElute Mammalian Genomic DNA Miniprep Kit (Sigma-Aldrich). Once extracted and fragmented, either targeted or untargeted sequencing can be done to determine the sample's genotypes at loci. For example, whole genome, whole transcriptome, or whole exome sequencing can be done to determine genotypes at millions or even billions of base pairs (i.e., base pairs can be "loci" to be evaluated).

In some cases, targeted sequencing of known polymorphic loci (e.g., SNPs and surrounding sequences) can be done as an alternative to microarray analysis. For example, the genomic DNA can be enriched for those fragments containing a locus (e.g., SNP location) to be analyzed using kits designed for this purpose (e.g., Agilent SureSelect, Illumina TruSeq Capture, and Nimblegen SeqCap EZ Choice). For example, genomic DNA containing the loci to be analyzed can be hybridized to biotinylated capture RNA fragments to form biotinylated RNA/genomic DNA complexes. Alternatively, DNA capture probes may be utilized resulting in the formation of biotinylated DNA/genomic DNA hybrids. Streptavidin coated magnetic beads and a magnetic force can be used to separate the biotinylated RNA/genomic DNA complexes from those genomic DNA fragments not present within a biotinylated RNA/genomic DNA complex. The obtained biotinylated RNA/genomic DNA complexes can be treated to remove the captured RNA from the magnetic beads, thereby leaving intact genomic DNA fragments containing a locus to be analyzed. These intact genomic DNA fragments containing the loci to be analyzed can be amplified using, for example, PCR techniques. The amplified genomic DNA fragments can be sequenced using a high-throughput sequencing technology or a next-generation sequencing technology such as Illumina HiSeq, Illumina MiSeq, Life Technologies SoLID, or Roche's 454.

Figure 2:
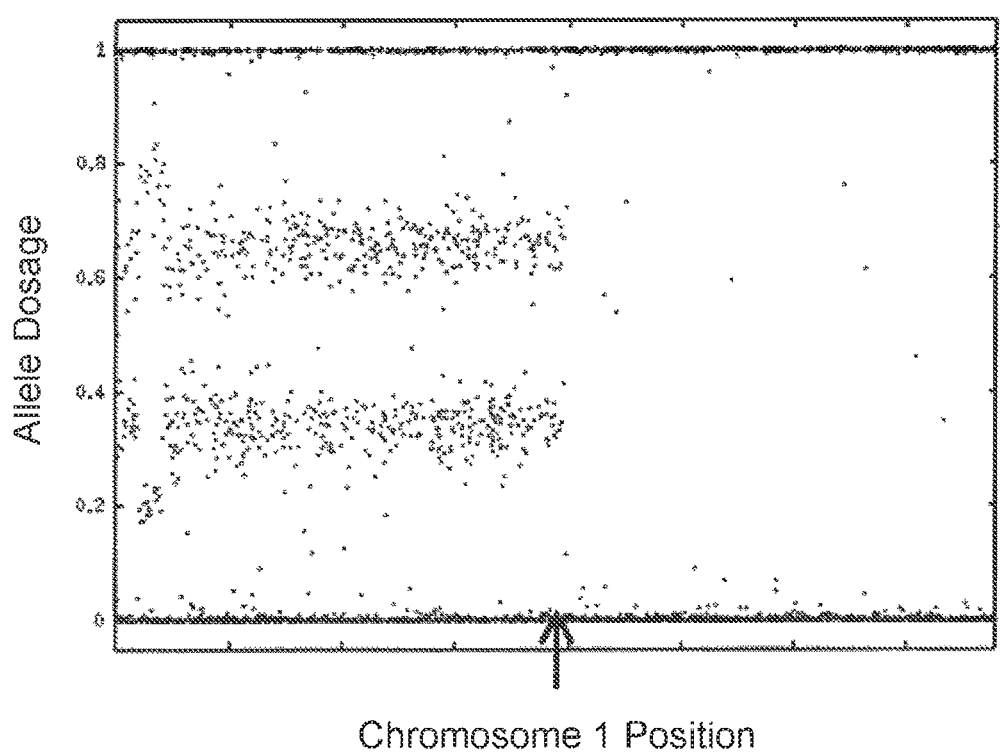
FIG. 2 is a graph plotting allele dosages of breast cancer cells for the same breast cancer patient as on FIG. 1 along chromosome 1 as determined using high-throughput sequencing. The arrow indicates a transition between a region of heterozygosity and an LOH region.

The sequencing results from the genomic DNA fragments can be used to identify loci as being homozygous or heterozygous, analogous to the microarray analysis described herein. In some cases, an analysis of the homozygous or heterozygous nature of loci over a length of a chromosome can be performed to determine the length of regions of homozygosity or heterozygosity. For example, a stretch of SNP locations that are spaced apart (e.g., spaced about 25 kb to about 100 kb apart) along a chromosome can be evaluated by sequencing, and the sequencing results used to determine not only the presence of a region of homozygosity along a chromosome but also the length of that LOH region. Obtained sequencing results can be used to generate a graph that plots allele dosages along a chromosome. Allele dosage $d_i$ for SNP i can be calculated from adjusted number of captured probes for two alleles ($A_i$ and $B_i$): $d_i = A_i/(A_i + B_i)$. An example of such a graph is presented in FIG. 2. Determining whether homozygosity is due to LOH (as opposed to homozygosity in the germline) can be performed as described herein.

In some cases, a selection process can be used to select loci (e.g., SNP loci) to be evaluated using an assay configured to identify loci as being homozygous or heterozygous (e.g., SNP array-based assays and sequencing-based assays). For example, any human SNP location can be selected for inclusion in a SNP array-based assay or a sequencing-based assay configured to identify loci as being homozygous or heterozygous within the genome of cells. In some cases, 0.5, 1.0, 1.5, 2.0, 2.5 million or more SNP locations present within the human genome can be evaluated to identify those SNPs that (a) are not present on the Y chromosome, (b) are not mitochondrial SNPs, (c) have a minor allele frequency of at least about five percent in Caucasians, (d) have a minor allele frequency of at least about one percent in three races other than Caucasians (e.g., Chinese, Japanese, and Yoruba), and/or (e) do not have a significant deviation from Hardy Weinberg equilibrium in any of the four races. In some cases, more than 100,000, 150,000, or 200,000 human SNPs can be selected that meet criteria (a) through (e). Of the human SNPs meeting criteria (a) through (e), a group of SNPs (e.g., top 110,000 SNPs) can be selected such that the SNPs have a high degree of allele frequency in Caucasians, cover the human genome in a somewhat evenly spaced manner (e.g., at least one SNP every about 25 kb to about 500 kb), and are not in linkage disequilibrium with another selected SNP for in any of the four races. In some cases, about 40, 50, 60, 70, 80, 90, 100, 110, 120, 130 thousand or more SNPs can be selected as meeting each of these criteria and included in an assay configured to identify LOH regions across a human genome. For example, between about 70,000 and about 90,000 (e.g., about 80,000) SNPs can be selected for analysis with a SNP array-based assay, and between about 45,000 and about 55,000 (e.g., about 54,000) SNPs can be selected for analysis with a sequencing-based assay.

As described herein, a cell sample can be assessed to determine if the genome of cells of the sample contains an LOH signature, lacks an LOH signature, has an increased number of LOH regions that cover the whole chromosome, or lacks an increased number of LOH regions that cover the whole chromosome. Any appropriate type of sample can be assessed. For example, a sample containing cancer cells can be assessed to determine if the genome of the cancer cells contains an LOH signature, lacks an LOH signature, has an increased number of LOH regions that cover the whole chromosome, or lacks an increased number of LOH regions that cover the whole chromosome. Examples of samples containing cancer cells that can be assessed as described herein include, without limitation, tumor biopsy samples (e.g., breast tumor biopsy samples), formalin-fixed, paraffin-embedded tissue samples containing cancer cells, core needle biopsies, fine needle aspirates, and samples containing cancer cells shed from a tumor (e.g., blood, urine or other bodily fluids). For formalin-fixed, paraffin-embedded tissue samples, the sample can be prepared by DNA extraction using a genomic DNA extraction kit optimized for FFPE tissue, including but not limited to those described above (e.g., QuickExtract FFPE DNA Extraction Kit (Epicentre), and QIAamp DNA FFPE Tissue Kit (Qiagen)).

In some cases, laser dissection techniques can be performed on a tissue sample to minimize the number of non-cancer cells within a cancer cell sample to be assessed. In some cases, antibody based purification methods can be used to enrich for cancer cells and/or deplete non-cancer cells. Examples of antibodies that could be used for cancer cell enrichment include, without limitation, anti-EpCAM, anti-TROP-2, anti-c-Met, anti-Folate binding protein, anti-N-Cadherin, anti-CD318, anti-antimesencymal stem cell antigen, anti-Her2, anti-MUC1, anti-EGFR, anti-cytokeratins (e.g., cytokeratin 7, cytokeratin 20, etc.), anti-Caveolin-1, anti-PSA, anti-CA125, and anti-surfactant protein antibodies.

Any type of cancer cell can be assessed using the methods and materials described herein. For example, breast cancer cells, ovarian cancer cells, liver cancer cells, esophageal cancer cells, lung cancer cells, head and neck cancer cells, prostate cancer cells, colon, rectal, or colorectal cancer cells, and pancreatic cancer cells can be assessed to determine if the genome of the cancer cells contains an LOH signature, lacks an LOH signature, has an increased number of LOH regions that cover the whole chromosome, or lacks an increased number of LOH regions that cover the whole chromosome.

When assessing the genome of cancer cells for the presence or absence of an LOH signature, one or more (e.g., one, two, three, four, five, six, seven, eight, nine, ten, eleven, twelve, 13, 14, 15, 16, 17, 18, 19, 20, 21, 22, or 23) pairs of chromosomes can be assessed. In some cases, the genome of cancer cells is assessed for the presence or absence of an LOH signature using one or more (e.g., one, two, three, four, five, six, seven, eight, nine, ten, eleven, twelve, 13, 14, 15, 16, 17, 18, 19, 20, 21, 22, 23) pairs of chromosomes.

In some cases, it can be helpful to exclude certain chromosomes from this analysis. For example, in the case of females, a pair to be assessed can include the pair of X sex chromosomes; whereas, in the case of males, a pair of any autosomal chromosomes (i.e., any pair other than the pair of X and Y sex chromosomes) can be assessed. As another example, in some cases the chromosome number 17 pair may be excluded from the analysis. It has been determined that certain chromosomes carry unusually high levels of LOH in certain cancers and, thus, it can be helpful to exclude such chromosomes when analyzing samples as described herein from patients having these cancers. In some cases, the sample is from a patient having ovarian cancer, and the chromosome to be excluded is chromosome 17.

When assessing the genome of cancer cells for the presence or absence of an increased number of LOH regions that cover the whole chromosome, 10 or more (e.g., 13, 16, 19 or 23) pairs of chromosomes can be assessed. In the case of females, a pair to be assessed can include the pair of X sex chromosomes; whereas, in the case of males, a pair of any autosomal chromosomes (i.e., any pair other than the pair of X and Y sex chromosomes) can be assessed. In some cases, the chromosome number 17 pair may be excluded from the analysis. In some cases, the sample is from a patient having ovarian cancer, and the chromosome to be excluded is chromosome 17. In some cases, the genome of cancer cells is assessed for the presence or absence of an increased number of LOH regions that cover the whole chromosome using 10 or more (e.g., 13, 16 19, or 23) pairs of chromosomes.

As described herein, patients having cancer cells identified as having a positive LOH signature status can be classified, based at least in part on a positive LOH signature status, as being likely to respond to a particular cancer treatment regimen. For example, patients having cancer cells with a genome containing an LOH signature can be classified, based at least in part on a positive LOH signature status, as being likely to respond to a cancer treatment regimen that includes the use of a DNA damaging agent, a PARP inhibitor, radiation, or a combination thereof. Examples of DNA damaging agents include, without limitation, platinum-based chemotherapy drugs (e.g., cisplatin, carboplatin, oxaliplatin, and picoplatin), anthracyclines (e.g., epirubicin and doxorubicin), topoisomerase I inhibitors (e.g., campothecin, topotecan, and irinotecan), and triazene compounds (e.g., dacarbazine and temozolomide). Examples of PARP inhibitors include, without limitation, olaparib, iniparib, and veliparib. Examples of information that can be used in addition to a positive LOH signature status to base a classification of being likely to respond to a particular cancer treatment regimen include, without limitation, previous treatment results, germline or somatic DNA mutations, gene or protein expression profiling (e.g., ER/PR/HER2 status, PSA levels), tumor histology (e.g., adenocarcinoma, squamous cell carcinoma, papillary serous carcinoma, mucinous carcinoma, invasive ductal carcinoma, ductal carcinoma insitu (non-invasive), etc.), disease stage, tumor or cancer grade (e.g., well, moderately, or poorly differentiated (e.g., Gleason, modified Bloom Richardson), etc.), number of previous courses of treatment, etc.

Once classified as being likely to respond to a particular cancer treatment regimen (e.g., a cancer treatment regimen that includes the use of a DNA damaging agent, a PARP inhibitor, radiation, or a combination thereof), the cancer patient can be treated with such a cancer treatment regimen. Any appropriate method for treating the cancer at issue can be used to treat a cancer patient identified as having cancer cells having a positive LOH signature status. For example, platinum-based chemotherapy drugs or a combination of platinum-based chemotherapy drugs can be used to treat cancer as described elsewhere (see, e.g., U.S. Pat. Nos. 3,892,790, 3,904,663, 7,759,510, 7,759,488 and 7,754,684. In some cases, anthracyclines or a combination of anthracyclines can be used to treat cancer as described elsewhere (see, e.g., U.S. Pat. Nos. 3,590,028, 4,138,480, 4,950,738, 6,087,340, 7,868,040, and 7,485,707. In some cases, topoisomerase I inhibitors or a combination of topoisomerase I inhibitors can be used to treat cancer as described elsewhere (see, e.g., U.S. Pat. Nos. 5,633,016 and 6,403,563. In some cases, PARP inhibitors or a combination of PARP inhibitors can be used to treat cancer as described elsewhere (see, e.g., U.S. Pat. Nos. 5,177,075, 7,915,280, and 7,351,701. In some cases, radiation can be used to treat cancer as described elsewhere (see, e.g., U.S. Pat. No. 5,295,944). In some cases, a combination comprising different agents (e.g., a combination comprising any of platinum-based chemotherapy drugs, anthracyclines, topoisomerase I inhibitors, and/or PARP inhibitors) with or without radiation treatments can be used to treat cancer. In some cases, a combination treatment may comprise any of the above agents or treatments (e.g., a DNA damaging agent, a PARP inhibitor, radiation, or a combination thereof) together with another agent or treatment—e.g., a taxane agent (e.g., doxetaxel, paclitaxel, abraxane), a growth factor or growth factor receptor inhibitor (e.g., erlotinib, gefitinib, lapatinib, sunitinib, bevacizumab, cetuximab, trastuzumab, panitumumab), and/or an antimetabolite (e.g., 5-flourouracil, methotrexate).

In some cases, patients identified as having cancer cells with a genome lacking an LOH signature can be classified, based at least in part on a negative LOH signature status, as being less likely to respond to a treatment regimen that includes a DNA damaging agent, a PARP inhibitor, radiation, or a combination thereof. In turn, such a patient can be classified as likely to respond to a cancer treatment regimen that includes the use of one or more cancer treatment agents not associated with HDR, such as a taxane agent (e.g., doxetaxel, paclitaxel, abraxane), a growth factor or growth factor receptor inhibitor (e.g., erlotinib, gefitinib, lapatinib, sunitinib, bevacizumab, cetuximab, trastuzumab, panitumumab), and/or an antimetabolite agent (e.g., 5-flourouracil, methotrexate). Once classified as being likely to respond to a particular cancer treatment regimen (e.g., a cancer treatment regimen that includes the use of a cancer treatment agent not associated with HDR), the cancer patient can be treated with such a cancer treatment regimen. Any appropriate method for the cancer being treated can be used to treat a cancer patient identified as having cancer cells having a negative LOH signature status. Examples of information that can be used in addition to a negative LOH signature status to base a classification of being likely to respond to a particular cancer treatment regimen include, without limitation, previous treatment results, germline or somatic DNA mutations, gene or protein expression profiling (e.g., ER/PR/HER2 status, PSA levels), tumor histology (e.g., adenocarcinoma, squamous cell carcinoma, papillary serous carcinoma, mucinous carcinoma, invasive ductal carcinoma, ductal carcinoma in situ (non-invasive), etc.), disease stage, tumor or cancer grade (e.g., well, moderately, or poorly differentiated (e.g., Gleason, modified Bloom Richardson), etc.), number of previous courses of treatment, etc.

Once treated for a particular period of time (e.g., between one to six months), the patient can be assessed to determine whether or not the treatment regimen has an effect. If a beneficial effect is detected, the patient can continue with the same or a similar cancer treatment regimen. If a minimal or no beneficial effect is detected, then adjustments to the cancer treatment regimen can be made. For example, the dose, frequency of administration, or duration of treatment can be increased. In some cases, additional anti-cancer agents can be added to the treatment regimen or a particular anti-cancer agent can be replaced with one or more different anti-cancer agents. The patient being treated can continue to be monitored as appropriate, and changes can be made to the cancer treatment regimen as appropriate.

As described herein, this document provides methods for assessing patients for cells (e.g., cancer cells) having a genome containing an LOH signature. For example, one or more clinicians or medical professionals can determine if a patient contains cancer cells having a genome containing an LOH signature. In some cases, one or more clinicians or medical professionals can determine if a patient contains cancer cells having a genome containing an LOH signature by obtaining a cancer cell sample from the patient and assessing the genome of cancer cells of the cancer cell sample to determine the presence or absence of an LOH signature as described herein.

In some cases, one or more clinicians or medical professionals can obtain a cancer cell sample from a patient and provide that sample to a testing laboratory having the ability to assess the genome of cancer cells of the cancer cell sample to provide an indication about the presence or absence of an LOH signature as described herein. In such cases, the one or more clinicians or medical professionals can determine if a patient contains cancer cells having a genome containing an LOH signature by receiving information about the presence or absence of an LOH signature directly or indirectly from the testing laboratory. For example, a testing laboratory, after assessing the genome of cancer cells for presence or absence of an LOH signature as described herein, can provide a clinician or medical professional with, or access to, a written, electronic, or oral report or medical record that provides an indication about the presence or absence of an LOH signature for a particular patient being assessed. Such a written, electronic, or oral report or medical record can allow the one or more clinicians or medical professionals to determine if a particular patient being assessed contains cancer cells having a genome containing an LOH signature.

Once a clinician or medical professional or group of clinicians or medical professionals determines that a particular patient being assessed contains cancer cells having a genome containing an LOH signature, the clinician or medical professional (or group) can classify that patient as having cancer cells whose genome contains the presence of an LOH signature. In some cases, a clinician or medical professional or group of clinicians or medical professionals can diagnose a patient determined to have cancer cells whose genome contains the presence of an LOH signature as having cancer cells likely to be deficient in HDR. Such a diagnosis can be based solely on a determination that a particular patient being assessed contains cancer cells having a genome containing an LOH signature or can be based at least in part on a determination that a particular patient being assessed contains cancer cells having a genome containing an LOH signature. For example, a patient determined to have cancer cells whose genome contains the presence of an LOH signature can be diagnosed as likely to be deficient in HDR based on the combination of a positive LOH signature status and deficient status in one or more tumor suppressor genes (e.g., BRCA1/2, RAD51), a family history of cancer, or the presence of behavioral risk factors (e.g., smoking).

In some cases, a clinician or medical professional or group of clinicians or medical professionals can diagnose a patient determined to have cancer cells whose genome contains the presence of an LOH signature as having cancer cells likely to contain genetic mutations in one or more genes in the HDR pathway. Such a diagnosis can be based solely on a determination that a particular patient being assessed contains cancer cells having a genome containing an LOH signature or can be based at least in part on a determination that a particular patient being assessed contains cancer cells having a genome containing an LOH signature. For example, a patient determined to have cancer cells whose genome contains the presence of an LOH signature can be diagnosed as having cancer cells likely to contain genetic mutations in one or more genes in the HDR pathway based on the combination of a positive LOH positive status and a family history of cancer, or the presence of behavioral risk factors (e.g., smoking).

In some cases, a clinician or medical professional or group of clinicians or medical professionals can diagnose a patient determined to have cancer cells whose genome contains the presence of an LOH signature as having cancer cells likely to respond to a particular cancer treatment regimen. Such a diagnosis can be based solely on a determination that a particular patient being assessed contains cancer cells having a genome containing an LOH signature or can be based at least in part on a determination that a particular patient being assessed contains cancer cells having a genome containing an LOH signature. For example, a patient determined to have cancer cells whose genome contains the presence of an LOH signature can be diagnosed as being likely to respond to a particular cancer treatment regimen based on the combination of a positive LOH signature status and deficient status in one or more tumor suppressor genes (e.g., BRCA1/2, RAD51), a family history of cancer, or the presence of behavioral risk factors (e.g., smoking). As described herein, a patient determined to have cancer cells whose genome contains the presence of an LOH signature can be diagnosed as likely to respond to a cancer treatment regimen that includes the use of a platinum-based chemotherapy drug such as cisplatin, carboplatin, oxaliplatin, or picoplatin, an anthracycline such as epirubicin or doxorubicin, a topoisomerase I inhibitor such as campothecin, topotecan, or irinotecan, a PARP inhibitor, radiation, a combination thereof, or a combination of any of the preceding with another anti-cancer agent.

Once a clinician or medical professional or group of clinicians or medical professionals determines that a particular patient being assessed contains cancer cells having a genome lacking an LOH signature, the clinician or medical professional (or group) can classify that patient as having cancer cells whose genome contains an absence of an LOH signature. In some cases, a clinician or medical professional or group of clinicians or medical professionals can diagnose a patient determined to have cancer cells containing a genome that lacks the presence of an LOH signature as having cancer cells likely to have functional HDR. In some cases, a clinician or medical professional or group of clinicians or medical professionals can diagnose a patient determined to have cancer cells containing a genome that lacks the presence of an LOH signature as having cancer cells that do not likely contain genetic mutations in one or more genes in the HDR pathway. In some cases, a clinician or medical professional or group of clinicians or medical professionals can diagnose a patient determined to have cancer cells containing a genome that lacks the presence of an LOH signature or contains an increased number of LOH regions that cover the whole chromosome as having cancer cells that are less likely to respond to a platinum-based chemotherapy drug such as cisplatin, carboplatin, oxalaplatin, or picoplatin, an anthracycline such as epirubincin or doxorubicin, a topoisomerase I inhibitor such as campothecin, topotecan, or irinotecan, a PARP inhibitor, or radiation and/or more likely to respond to a cancer treatment regimen that includes the use of a cancer treatment agent not associated with HDR such as one or more taxane agents, growth factor or growth factor receptor inhibitors, anti-metabolite agents, etc.

As described herein, this document also provides methods for performing a diagnostic analysis of a nucleic acid sample (e.g., a genomic nucleic acid sample or amplified genomic nucleic acid sample) of a cancer patient to determine if cancer cells within the patient have a genome containing an LOH signature and/or an increased number of LOH regions that cover the whole chromosome. For example, one or more laboratory technicians or laboratory professionals can detect the presence or absence of an LOH signature in the genome of cancer cells of the patient or the presence or absence of an increased number of LOH regions that cover the whole chromosome in the genome of cancer cells of the patient. In some cases, one or more laboratory technicians or laboratory professionals can detect the presence or absence of an LOH signature or the presence or absence of an increased number of LOH regions that cover the whole chromosome in the genome of cancer cells of the patient by (a) receiving a cancer cell sample obtained from the patient, receiving a genomic nucleic acid sample obtained from cancer cells obtained from the patient, or receiving an enriched and/or amplified genomic nucleic acid sample obtained from cancer cells obtained from the patient and (b) performing an analysis (e.g., a SNP array-based assay or a sequencing-based assay) using the received material to detect the presence or absence of an LOH signature or the presence or absence of an increased number of LOH regions that cover the whole chromosome as described herein. In some cases, one or more laboratory technicians or laboratory professionals can receive a sample to be analyzed (e.g., a cancer cell sample obtained from the patient, a genomic nucleic acid sample obtained from cancer cells obtained from the patient, or an enriched and/or amplified genomic nucleic acid sample obtained from cancer cells obtained from the patient) directly or indirectly from a clinician or medical professional.

Once a laboratory technician or laboratory professional or group of laboratory technicians or laboratory professionals detects the presence of an LOH signature as described herein, the laboratory technician or laboratory professional (or group) can identify the patient whose cancer cells were detected as having an LOH signature as having cancer cells with a positive LOH signature status. For example, one or more laboratory technicians or laboratory professionals can identify a patient having cancer cells that were detected to have an LOH signature as having cancer cells with a positive LOH signature status by associating that positive LOH signature status or the result (or results or a summary of results) of the performed diagnostic analysis with the corresponding patient's name, medical record, symbolic/numerical identifier, or a combination thereof. In some cases, a laboratory technician or laboratory professional or group of laboratory technicians or laboratory professionals can identify a patient having cancer cells that were detected to have an LOH signature as having cancer cells potentially deficient in HDR by associating the positive LOH signature status, the potentially deficient in HDR status, or the result (or results or a summary of results) of the performed diagnostic analysis with the corresponding patient's name, medical record, symbolic/numerical identifier, or a combination thereof. Such identification can be based solely on detecting the presence of an LOH signature or can be based at least in part on detecting the presence of an LOH signature. For example, a laboratory technician or laboratory professional can identify a patient having cancer cells that were detected to have an LOH signature as having cancer cells potentially deficient in HDR based on a combination of a positive LOH signature status and the results of other genetic and biochemical tests performed at the testing laboratory.

In some cases, a laboratory technician or laboratory professional or group of laboratory technicians or laboratory professionals can identify a patient having cancer cells that were detected to have an LOH signature as having cancer cells potentially containing a genetic mutation in one or more genes in the HDR pathway by associating the positive LOH signature status, the potential presence of a genetic mutation in one or more genes in the HDR pathway, or the result (or results or a summary of results) of the performed diagnostic analysis with the corresponding patient's name, medical record, symbolic/numerical identifier, or a combination thereof. Such identification can be based solely on detecting the presence of an LOH signature or can be based at least in part on detecting the presence of an LOH signature. For example, a laboratory technician or laboratory professional can identify a patient having cancer cells that were detected to have an LOH signature as having cancer cells potentially containing a genetic mutation in one or more genes in the HDR pathway based on a combination of a positive LOH signature status and the results of other genetic and biochemical tests performed at the testing laboratory.

In some cases, a laboratory technician or laboratory professional or group of laboratory technicians or laboratory professionals can identify a patient having cancer cells that were detected to have an LOH signature as having cancer cells likely to respond to a particular cancer treatment regimen by associating the positive LOH signature status, a potentially deficient HDR status, a potential presence of a deficient status in one or more genes in the HDR pathway, or the result (or results or a summary of results) of the performed diagnostic analysis with the corresponding patient's name, medical record, symbolic/numerical identifier, or a combination thereof. Such identification can be based solely on detecting the presence of an LOH signature or can be based at least in part on detecting the presence of an LOH signature. For example, a laboratory technician or laboratory professional can identify a patient having cancer cells that were detected to have an LOH signature as having cancer cells likely to respond to a particular cancer treatment regimen based on a combination of a positive LOH signature status and the results of other genetic and biochemical tests performed at the testing laboratory.

Once a laboratory technician or laboratory professional or group of laboratory technicians or laboratory professionals detects the absence of an LOH signature, the laboratory technician or laboratory professional (or group) can identify the patient whose cancer cells were detected as lacking an LOH signature as having cancer cells with a negative LOH signature status. For example, one or more laboratory technicians or laboratory professionals can identify a patient having cancer cells that were detected to lack an LOH signature as having cancer cells with a negative LOH signature status by associating that negative LOH signature status or the result (or results or a summary of results) of the performed diagnostic analysis with the corresponding patient's name, medical record, symbolic/numerical identifier, or a combination thereof. In some cases, a laboratory technician or laboratory professional or group of laboratory technicians or laboratory professionals can identify a patient having cancer cells that were detected to lack an LOH signature as having cancer cells with potentially intact HDR by associating the negative LOH signature status, the potentially intact HDR status, or the result (or results or a summary of results) of the performed diagnostic analysis with the corresponding patient's name, medical record, symbolic/numerical identifier, or a combination thereof.

In some cases, a laboratory technician or laboratory professional or group of laboratory technicians or laboratory professionals can identify a patient having cancer cells that were detected to lack an LOH signature as having cancer cells with potentially intact genes of the HDR pathway by associating the negative LOH signature status, the potential absence of genetic mutations in genes of the HDR pathway, or the result (or results or a summary of results) of the performed diagnostic analysis with the corresponding patient's name, medical record, symbolic/numerical identifier, or a combination thereof.

In some cases, a laboratory technician or laboratory professional or group of laboratory technicians or laboratory professionals can identify a patient having cancer cells that were detected to lack an LOH signature as having cancer cells as less likely to respond to one particular treatment (e.g., a platinum-based chemotherapy drug such as cisplatin, carboplatin, oxalaplatin, or picoplatin, an anthracycline such as epirubincin or doxorubicin, a topoisomerase I inhibitor such as campothecin, topotecan, or irinotecan, a PARP inhibitor such as iniparib, olaparib, or velapirib, or radiation) and/or more likely to respond to a particular cancer treatment regimen (e.g., a cancer treatment regimen that includes the use of a cancer treatment agent not associated with HDR) by associating the negative LOH signature status, a potentially intact HDR status, a potential absence of genetic mutations in genes of the HDR pathway, or the result (or results or a summary of results) of the performed diagnostic analysis with the corresponding patient's name, medical record, symbolic/numerical identifier, or a combination thereof.

Once a laboratory technician or laboratory professional or group of laboratory technicians or laboratory professionals detects the presence of an increased number of LOH regions that cover the whole chromosome, the laboratory technician or laboratory professional (or group) can identify the patient whose cancer cells were detected as having an increased number of LOH regions that cover the whole chromosome as likely having cancer cells with an intact BRCA1 and BRCA2 status. For example, one or more laboratory technicians or laboratory professionals can identify a patient having cancer cells that were detected to have an increased number of LOH regions that cover the whole chromosome as likely having cancer cells with an intact BRCA1 and BRCA2 status by associating the presence of an increased number of LOH regions that cover the whole chromosome or the result (or results or a summary of results) of the performed diagnostic analysis with the corresponding patient's name, medical record, symbolic/numerical identifier, or a combination thereof.

Figure 15:
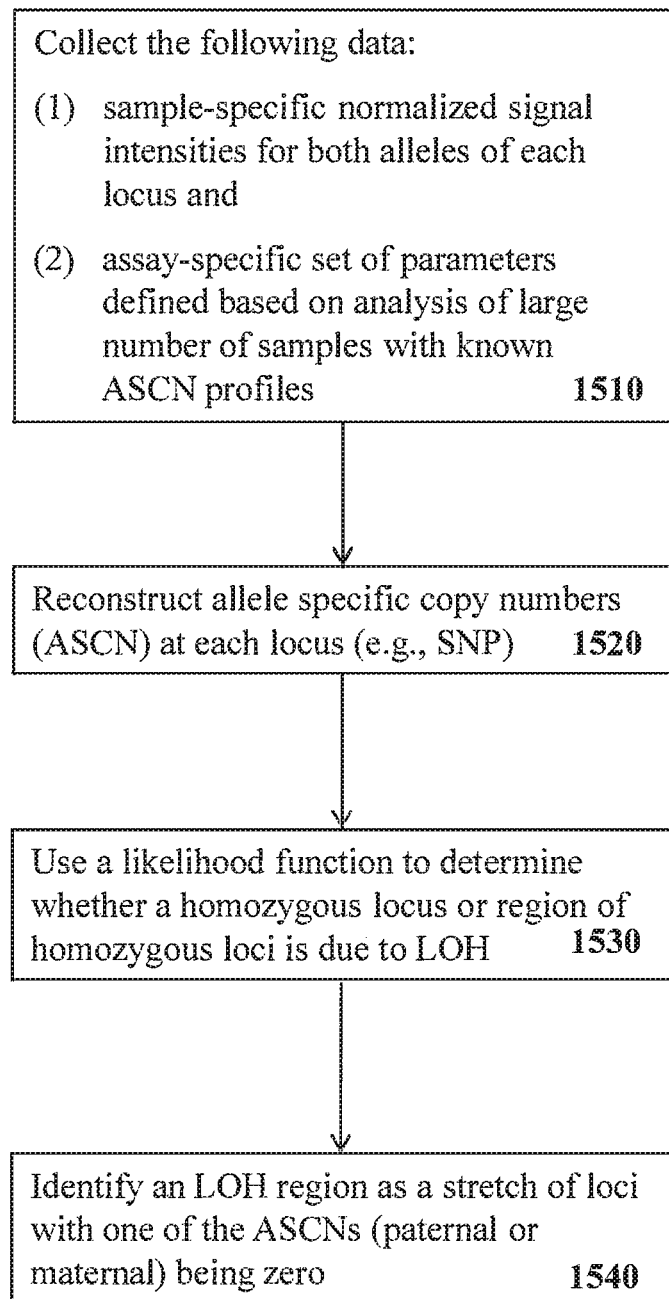
FIG. 15 is a flow chart of an example computational process for identifying LOH loci and regions.

FIG. 15 shows an exemplary process by which a computing system (or a computer program (e.g., software) containing computer-executable instructions) can identify LOH loci or regions from genotype data as described herein. If the observed ratio of the signals of two alleles, A and B, is two to one, there are two possibilities. The first possibility is that cancer cells have LOH with deletion of allele B in a sample with 50% contamination with normal cells. The second possibility is that there is no LOH but allele A is duplicated in a sample with no contamination with normal cells. The process begins at box 1500, where the following data are collected by the computing system; (1) sample-specific normalized signal intensities for both alleles of each locus and (2) assay-specific (specific for different SNP arrays and for sequence based approach) set of parameters defined based on analysis of large number of samples with known ASCN profiles. As described herein, any appropriate assay such as a SNP array-based assay or sequencing-based assay can be used to assess loci along a chromosome for homozygosity or heterozygosity. In some cases, a system including a signal detector and a computer can be used to collect data (e.g., fluorescent signals or sequencing results) regarding the homozygous or heterozygous nature of the plurality of loci (e.g., sample-specific normalized signal intensities for both alleles of each locus). At box 1510, allele specific copy numbers (ASCN) are reconstructed at each locus (e.g., each SNP). ASCNs are the numbers of copies of both paternal and maternal alleles. At box 1530, a likelihood function is used to determine whether a homozygous locus or region of homozygous loci is due to LOH. This can be conceptually analogous to a previously described algorithm designed to reconstruct total copy number (rather than ASCN) at each locus (e.g., SNP). See International Application No. PCT/US2011/026098 to Abkevish et al. The likelihood function can be maximized over ASCN of all loci, level of contamination with benign tissue, total copy number averaged over the whole genome, and sample specific noise level. At box 1540, an LOH region is determined as a stretch of SNPs with one of the ASCNs (paternal or maternal) being zero.

Figure 3:
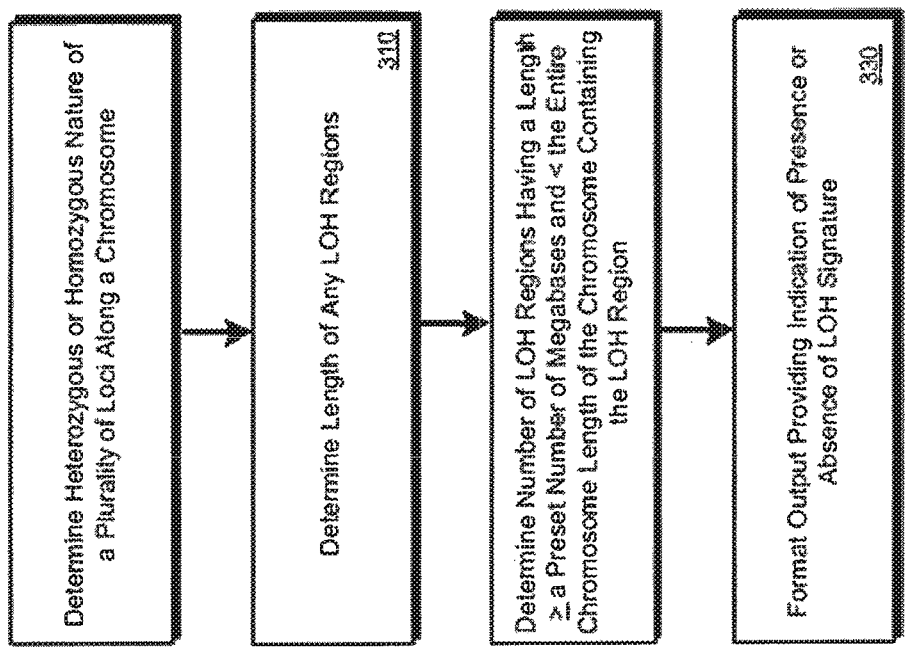
FIG. 3 is a flow chart of an example process for assessing the genome of a cell (e.g., a cancer cell) for an LOH signature.

FIG. 3 shows an exemplary process by which a computing system can determine the presence or absence of an LOH signature. The process begins at box 300, where data regarding the homozygous or heterozygous nature of a plurality of loci along a chromosome is collected by the computing system. As described herein, any appropriate assay such as a SNP array-based assay or sequencing-based assay can be used to assess loci along a chromosome for homozygosity or heterozygosity. In some cases, a system including a signal detector and a computer can be used to collect data (e.g., fluorescent signals or sequencing results) regarding the homozygous or heterozygous nature of the plurality of loci. At box 310, data regarding the homozygous or heterozygous nature of a plurality of loci as well as the location or spatial relationship of each locus is assessed by the computing system to determine the length of any LOH regions present along a chromosome. At box 320, data regarding the number of LOH regions detected and the length of each detected LOH region is assessed by the computing system to determine the number of LOH regions that have a length (a) greater than or equal to a preset number of Mb (e.g., 15 Mb) and (b) less than the entire length of the chromosome containing that LOH region. At box 330, the computing system formats an output providing an indication of the presence or absence of an LOH signature. Once formatted, the computing system can present the output to a user (e.g., a laboratory technician, clinician, or medical professional). As described herein, the presence or absence of an LOH signature can be used to provide an indication about a patient's likely HDR status, an indication about the likely presence or absence of genetic mutations in genes of the HDR pathway, and/or an indication about possible cancer treatment regimens.

Figure 4:
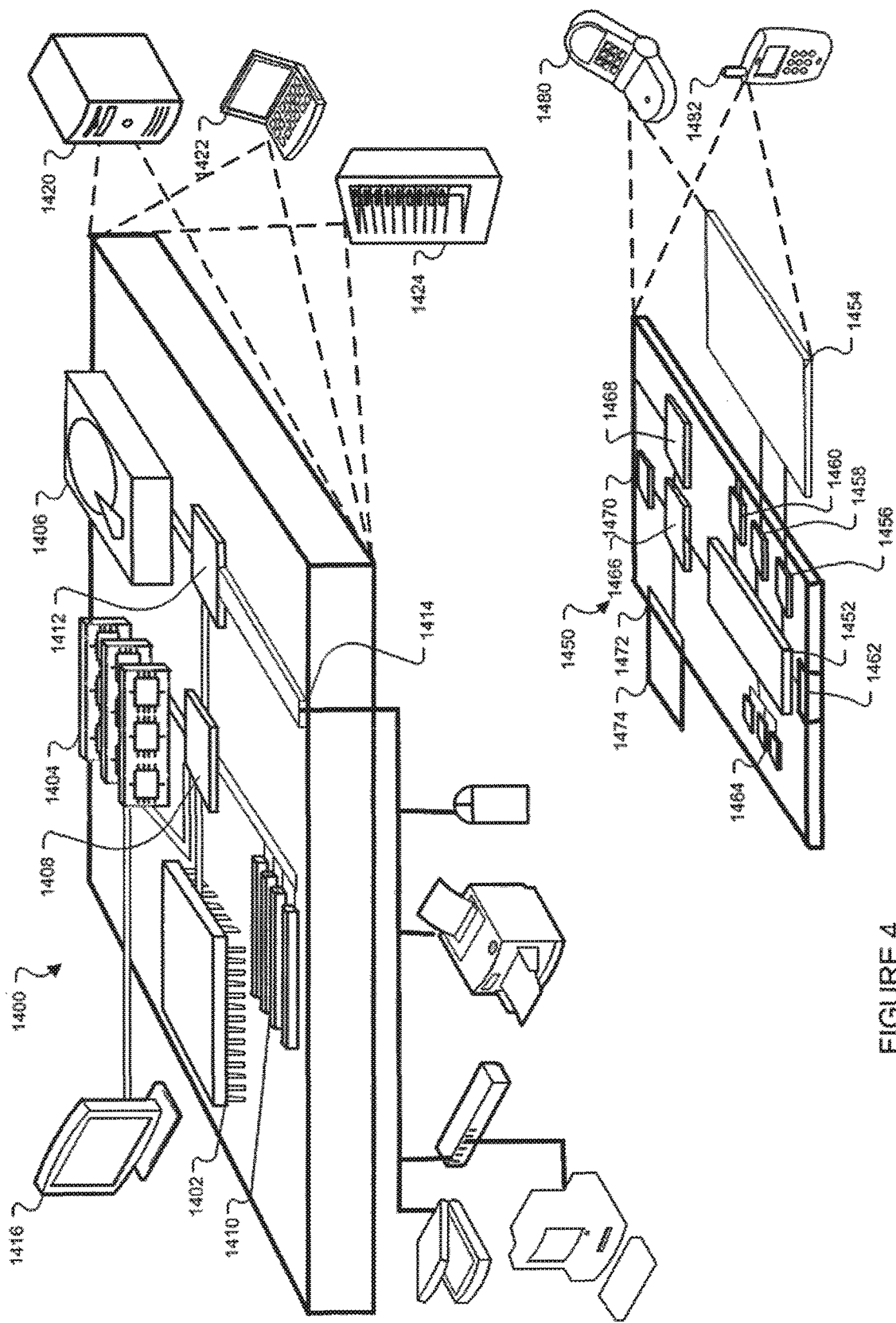
FIG. 4 is a diagram of an example of a computer device and a mobile computer device that can be used to implement the techniques described herein.

FIG. 4 is a diagram of an example of a computer device 1400 and a mobile computer device 1450, which may be used with the techniques described herein. Computing device 1400 is intended to represent various forms of digital computers, such as laptops, desktops, workstations, personal digital assistants, servers, blade servers, mainframes, and other appropriate computers. Computing device 1450 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the inventions described and/or claimed in this document.

Computing device 1400 includes a processor 1402, memory 1404, a storage device 1406, a high-speed interface 1408 connecting to memory 1404 and high-speed expansion ports 1410, and a low speed interface 1415 connecting to low speed bus 1414 and storage device 1406. Each of the components 1402, 1404, 1406, 1408, 1410, and 1415, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as display 1416 coupled to high speed interface 1408. In other implementations, multiple processors and/or multiple buses may be used, as appropriate, along with multiple memories and types of memory. Also, multiple computing devices 1400 may be connected, with each device providing portions of the necessary operations (e.g., as a server bank, a group of blade servers, or a multi-processor system).

The memory 1404 stores information within the computing device 1400. In one implementation, the memory 1404 is a volatile memory unit or units. In another implementation, the memory 1404 is a non-volatile memory unit or units. The memory 1404 may also be another form of computer-readable medium, such as a magnetic or optical disk.

The storage device 1406 is capable of providing mass storage for the computing device 1400. In one implementation, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described herein. The information carrier is a computer- or machine-readable medium, such as the memory 1404, the storage device 1406, memory on processor 1402, or a propagated signal.

The high speed controller 1408 manages bandwidth-intensive operations for the computing device 1400, while the low speed controller 1415 manages lower bandwidth-intensive operations. Such allocation of functions is exemplary only. In one implementation, the high-speed controller 1408 is coupled to memory 1404, display 1416 (e.g., through a graphics processor or accelerator), and to high-speed expansion ports 1410, which may accept various expansion cards (not shown). In the implementation, low-speed controller 1415 is coupled to storage device 1406 and low-speed expansion port 1414. The low-speed expansion port, which may include various communication ports (e.g., USB, Bluetooth, Ethernet, or wireless Ethernet) may be coupled to one or more input/output devices, such as a keyboard, a pointing device, a scanner, an optical reader, a fluorescent signal detector, or a networking device such as a switch or router, e.g., through a network adapter.

The computing device 1400 may be implemented in a number of different forms, as shown in the figure. For example, it may be implemented as a standard server 1420, or multiple times in a group of such servers. It may also be implemented as part of a rack server system 1424. In addition, it may be implemented in a personal computer such as a laptop computer 1422. Alternatively, components from computing device 1400 may be combined with other components in a mobile device (not shown), such as device 1450. Each of such devices may contain one or more of computing device 1400, 1450, and an entire system may be made up of multiple computing devices 1400, 1450 communicating with each other.

Computing device 1450 includes a processor 1452, memory 1464, an input/output device such as a display 1454, a communication interface 1466, and a transceiver 1468, among other components (e.g., a scanner, an optical reader, a fluorescent signal detector). The device 1450 may also be provided with a storage device, such as a microdrive or other device, to provide additional storage. Each of the components 1450, 1452, 1464, 1454, 1466, and 1468, are interconnected using various buses, and several of the components may be mounted on a common motherboard or in other manners as appropriate.

The processor 1452 can execute instructions within the computing device 1450, including instructions stored in the memory 1464. The processor may be implemented as a chipset of chips that include separate and multiple analog and digital processors. The processor may provide, for example, for coordination of the other components of the device 1450, such as control of user interfaces, applications run by device 1450, and wireless communication by device 1450.

Processor 1452 may communicate with a user through control interface 1458 and display interface 1456 coupled to a display 1454. The display 1454 may be, for example, a TFT LCD (Thin-Film-Transistor Liquid Crystal Display) or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may be provide in communication with processor 1452, so as to enable near area communication of device 1450 with other devices. External interface 1462 may provide, for example, for wired communication in some implementations, or for wireless communication in other implementations, and multiple interfaces may also be used.

The memory 1464 stores information within the computing device 1450. The memory 1464 can be implemented as one or more of a computer-readable medium or media, a volatile memory unit or units, or a non-volatile memory unit or units. Expansion memory 1474 may also be provided and connected to device 1450 through expansion interface 1472, which may include, for example, a SIMM (Single In Line Memory Module) card interface. Such expansion memory 1474 may provide extra storage space for device 1450, or may also store applications or other information for device 1450. For example, expansion memory 1474 may include instructions to carry out or supplement the processes described herein, and may include secure information also. Thus, for example, expansion memory 1474 may be provide as a security module for device 1450, and may be programmed with instructions that permit secure use of device 1450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described herein. The information carrier is a computer- or machine-readable medium, such as the memory 1464, expansion memory 1474, memory on processor 1452, or a propagated signal that may be received, for example, over transceiver 1468 or external interface 1462.

Device 1450 may communicate wirelessly through communication interface 1466, which may include digital signal processing circuitry where necessary. Communication interface 1466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1468. In addition, short-range communication may occur, such as using a Bluetooth, WiFi, or other such transceiver (not shown). In addition, GPS (Global Positioning System) receiver module 1470 may provide additional navigation- and location-related wireless data to device 1450, which may be used as appropriate by applications running on device 1450.

Device 1450 may also communicate audibly using audio codec 1460, which may receive spoken information from a user and convert it to usable digital information. Audio codec 1460 may likewise generate audible sound for a user, such as through a speaker, e.g., in a handset of device 1450. Such sound may include sound from voice telephone calls, may include recorded sound (e.g., voice messages, music files, etc.) and may also include sound generated by applications operating on device 1450.

The computing device 1450 may be implemented in a number of different forms, as shown in the figure. For example, it may be implemented as a cellular telephone 1480. It may also be implemented as part of a smartphone 1482, personal digital assistant, or other similar mobile device.

Various implementations of the systems and techniques described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, and Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described herein can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described herein can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described herein), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In some cases, a computing system provided herein can be configured to include one or more sample analyzers. A sample analyzer can be configured to produce a plurality of signals about genomic DNA of at least one pair of human chromosomes of a cancer cell. For example, a sample analyzer can produce signals that are capable of being interpreted in a manner that identifies the homozygous or heterozygous nature of loci along a chromosome. In some cases, a sample analyzer can be configured to carry out one or more steps of a SNP array-based assay or sequencing-based assay and can be configured to produce and/or capture signals from such assays. In some cases, a computing system provided herein can be configured to include a computing device. In such cases, the computing device can be configured to receive signals from a sample analyzer. The computing device can include computer-executable instructions or a computer program (e.g., software) containing computer-executable instructions for carrying out one or more of the methods or steps described herein. In some cases, such computer-executable instructions can instruct a computing device to analyze signals from a sample analyzer, from another computing device, from a SNP array-based assay, or from a sequencing-based assay. The analysis of such signals can be carried out to determine genotypes, homozygosity at certain loci, regions of homozygosity, the number of LOH regions, to determine the size of LOH regions, to determine the number of LOH regions having a particular size or range of sizes, to determine whether or not a sample is positive for an LOH signature, to determine the number of Indicator LOH Regions in at least one pair of human chromosomes, to determine a likelihood of a deficiency in BRCA1 and/or BRCA2 genes, to determine a likelihood of a deficiency in HDR, to determine a likelihood that a cancer patient will respond to a particular cancer treatment regimen (e.g., a regimen that includes a DNA damaging agent, an anthracycline, a topoisomerase I inhibitor, radiation, a PARP inhibitor, or a combination thereof), or to determine a combination of these items.

In some cases, a computing system provided herein can include computer-executable instructions or a computer program (e.g., software) containing computer-executable instructions for formatting an output providing an indication about the number of LOH regions, the size of LOH regions, the number of LOH regions having a particular size or range of sizes, whether or not a sample is positive for an LOH signature, the number of Indicator LOH Regions in at least one pair of human chromosomes, a likelihood of a deficiency in BRCA1 and/or BRCA2 genes, a likelihood of a deficiency in HDR, a likelihood that a cancer patient will respond to a particular cancer treatment regimen (e.g., a regimen that includes a DNA damaging agent, an anthracycline, a topoisomerase I inhibitor, radiation, a PARP inhibitor, or a combination thereof), or a combination of these items. In some cases, a computing system provided herein can include computer-executable instructions or a computer program (e.g., software) containing computer-executable instructions for determining a desired cancer treatment regimen for a particular patient based at least in part on the presence or absence of an LOH signature or on the number of Indicator LOH Regions.

In some cases, a computing system provided herein can include a pre-processing device configured to process a sample (e.g., cancer cells) such that a SNP array-based assay or sequencing-based assay can be performed. Examples of pre-processing devices include, without limitation, devices configured to enrich cell populations for cancer cells as opposed to non-cancer cells, devices configured to lyse cells and/or extract genomic nucleic acid, and devices configured to enrich a sample for particular genomic DNA fragments.

This document also provides kits for assessing samples (e.g., cancer cells) as described herein. For example, this document provides kits for assessing cancer cells for the presence of an LOH signature or to determine the number of Indicator LOH Regions in at least one pair of human chromosomes. A kit provided herein can include either SNP probes (e.g., an array of SNP probes for carrying out a SNP array-based assay described herein) or primers (e.g., primers designed for sequencing SNP regions via a sequencing-based assay) in combination with a computer program product containing computer-executable instructions for carrying out one or more of the methods or steps described herein (e.g., computer-executable instructions for determining the number of LOH regions having a particular size or range of sizes). In some cases, a kit provided herein can include at least 500, 1000, 10,000, 25,000, or 50,000 SNP probes capable of hybridizing to polymorphic regions of human genomic DNA. In some cases, a kit provided herein can include at least 500, 1000, 10,000, 25,000, or 50,000 primers capable of sequencing polymorphic regions of human genomic DNA. In some cases, a kit provided herein can include one or more other ingredients for performing a SNP array-based assay or a sequencing-based assay. Examples of such other ingredients include, without limitation, buffers, sequencing nucleotides, enzymes (e.g., polymerases), etc. This document also provides the use of any appropriate number of the materials provided herein in the manufacture of a kit for carrying out one or more of the methods or steps described herein. For example, this document provides the use of a collection of SNP probes (e.g., a collection of 10,000 to 100,000 SNP probes) and a computer program product provided herein in the manufacture of a kit for assessing cancer cells for the presence of an LOH signature. As another example, this document provides the use of a collection of primers (e.g., a collection of 10,000 to 100,000 primers for sequencing SNP regions) and a computer program product provided herein in the manufacture of a kit for assessing cancer cells for the presence of an LOH signature.

The invention will be further described in the following examples, which do not limit the scope of the invention described in the claims.

EXAMPLES

Example 1—Assessing LOH Regions and HDR

Two sets of tumors were used from advanced ovarian cancer patients. The first set of 94 tumors (training set) was used to derive a candidate signature, and the second set of 40 tumors (validation set) was used to validate the signature. All coding regions of BRCA1 and BRCA2 genes were sequenced to detect germ line and somatic mutations. Levels of BRCA1 and BRCA2 mRNA expression were measured, and Affymetrix SNP microarrays were performed.

A computer program was used to reconstruct LOH signature status based on allele intensities derived from the microarray data. An algorithm was developed and implemented as a computer program to reconstruct LOH regions based on genotype (e.g., SNP genotype) data.

One point of the algorithm was to first reconstruct allele specific copy numbers (ASCN) at each locus (e.g., SNP). ASCNs are the numbers of copies of both paternal and maternal alleles. An LOH region was then determined as a stretch of SNPs with one of the ASCNs (paternal or maternal) being zero. The algorithm was based on maximizing a likelihood function and was conceptually analogous to a previously described algorithm designed to reconstruct total copy number (rather than ASCN) at each locus (e.g., SNP). See International Application No. PCT/US2011/026098 to Abkevish et al. The likelihood function was maximized over ASCN of all loci, level of contamination with benign tissue, total copy number averaged over the whole genome, and sample specific noise level. The input data for the algorithm included (1) sample-specific normalized signal intensities for both allele of each locus and (2) assay-specific (specific for different SNP arrays and for sequence based approach) set of parameters defined based on analysis of large number of samples with known ASCN profiles.

Tumors were defined as being HDR deficient for the purpose of this analysis if they either had one or more deleterious mutations in BRCA1 and/or BRCA2 genes or if they had low expression of BRCA1 mRNA. The rest of the tumors were defined as likely HDR non-deficient for the purpose of this analysis.

Figure 5:
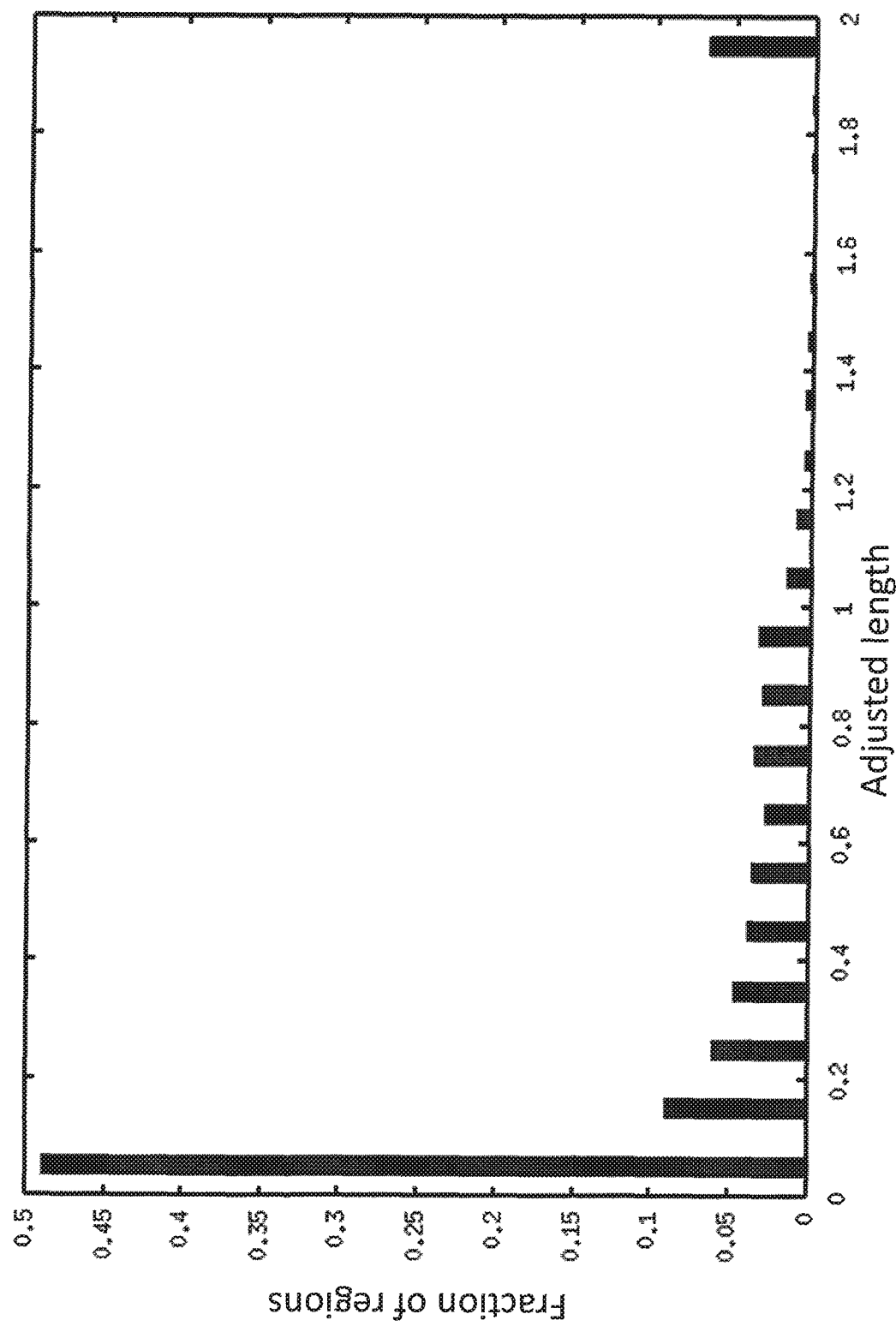
FIG. 5 is a graph plotting the length distribution of LOH regions detected in ovarian cancer cells from 62 human patients. The adjusted length refers to the fraction of chromosomes arms covered by LOH regions.
Figure 6:
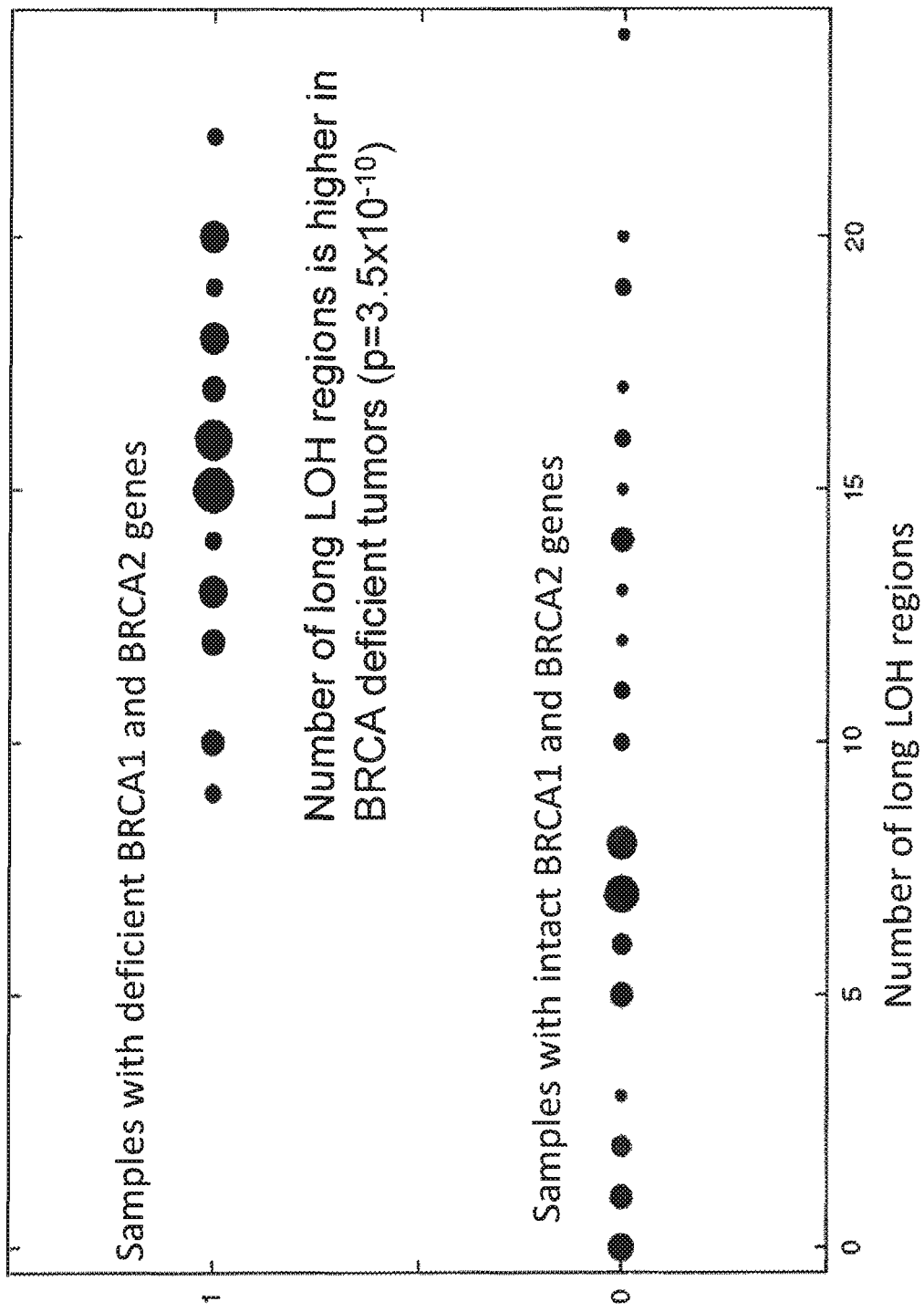
FIG. 6 is a graph plotting the number of LOH regions longer than 15 Mb and shorter than the entire chromosome for a training set of ovarian cancer cell samples with intact or deficient BRCA1 and BRCA2 genes. The size of the circles is proportional to the number of samples with such number of LOH regions.
Figure 7:
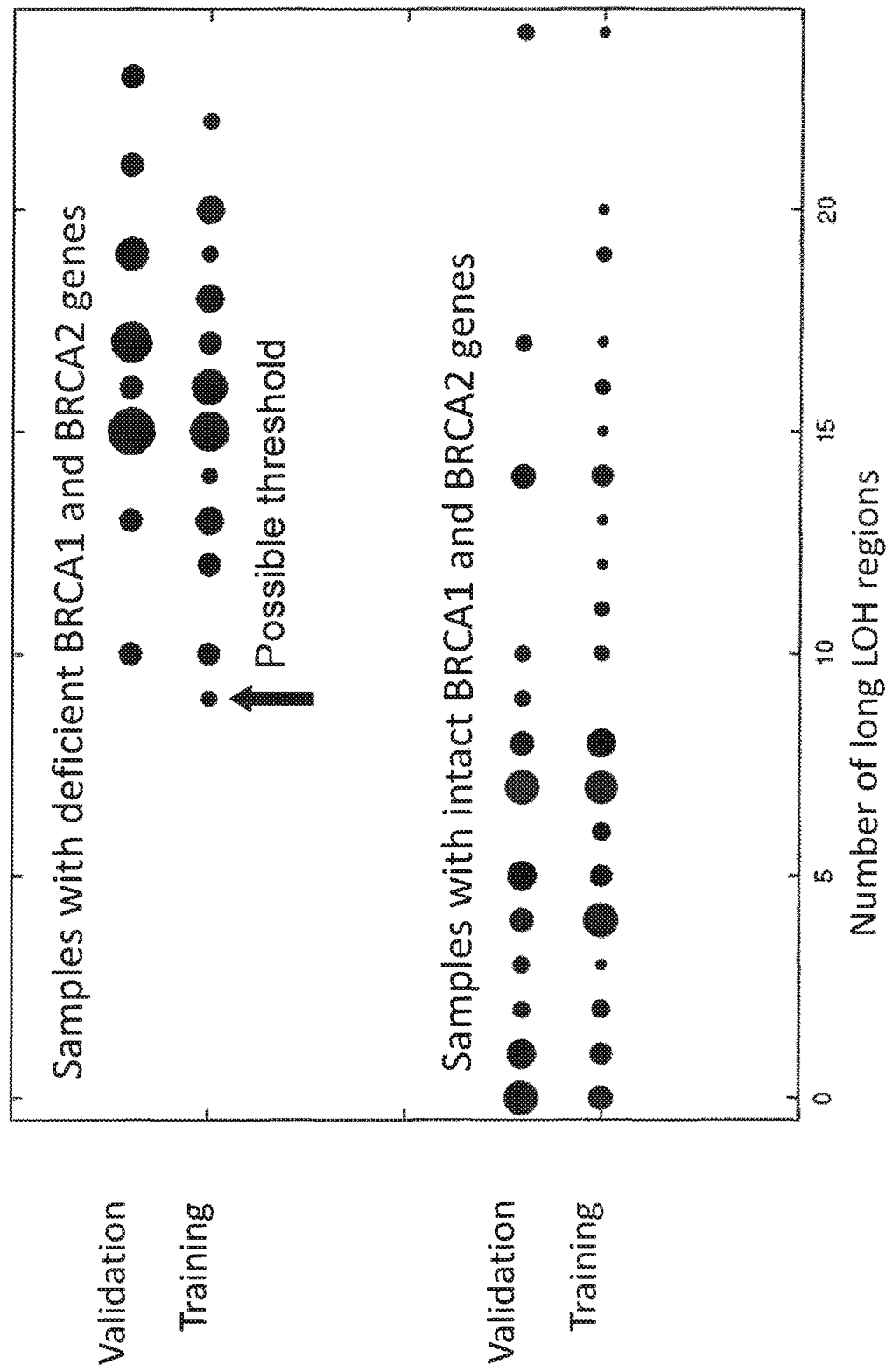
FIG. 7 is a graph plotting the number of LOH regions longer than 15 Mb and shorter than the entire chromosome for a training and validation sets of ovarian cancer cell samples with intact or deficient BRCA1 and BRCA2 genes. The size of the circles is proportional to the number of samples with such number of LOH regions.
Figure 8:
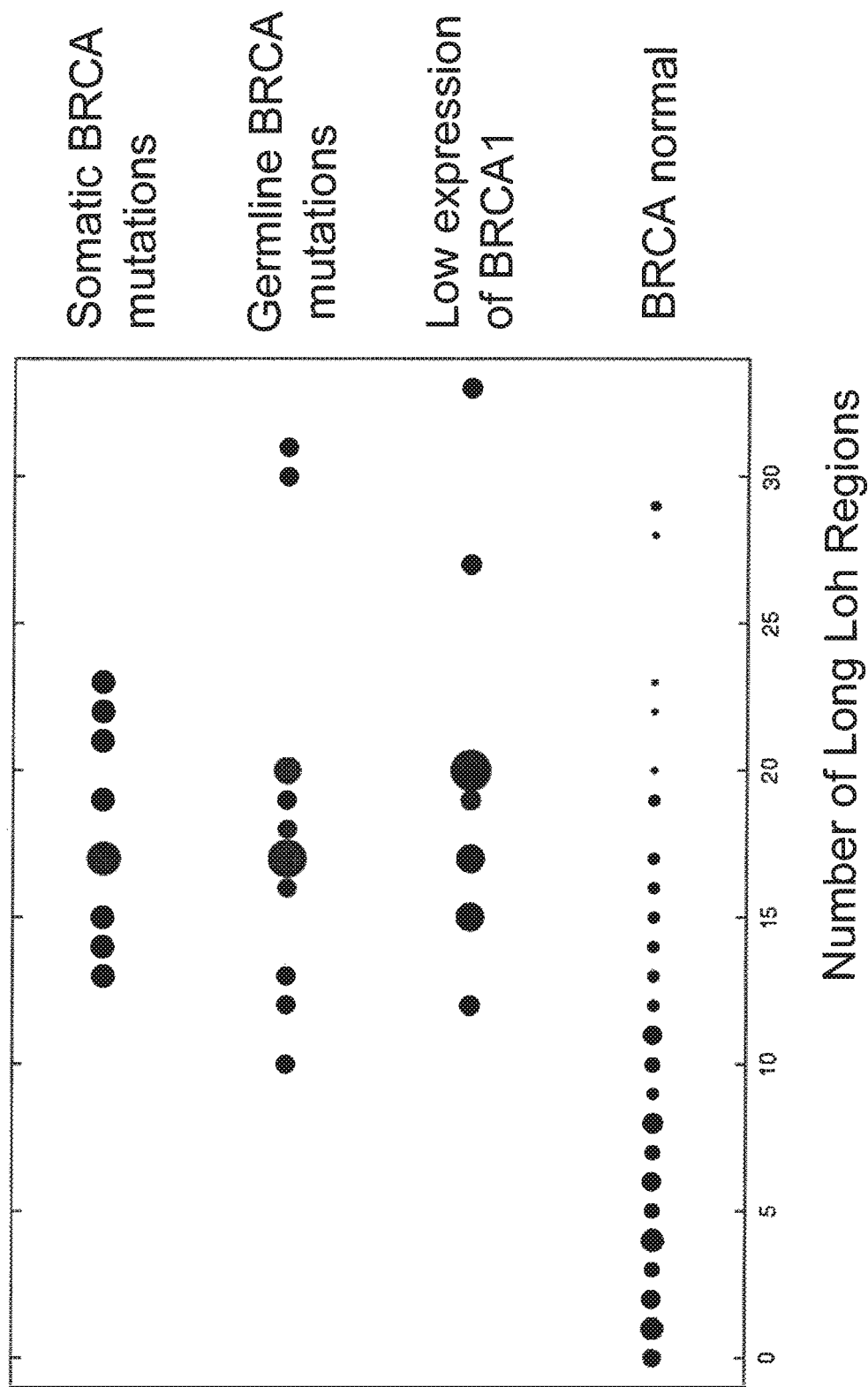
FIG. 8 is a graph plotting the number of LOH regions longer than 15 Mb and shorter than the entire chromosome for ovarian cancer cell samples with somatic BRCA mutations, with germline BRCA mutations, with low BRCA1 expression, or with intact BRCA (BRCA normal). The size of the circles is proportional to the number of samples with such number of LOH regions.

The distribution of the lengths of LOH regions was investigated (FIG. 5). Three categories of LOH regions were used: (1) LOH affecting a whole chromosome; (2) large LOH regions (greater than about 15 Mb), which typically affect a part of a chromosomal arm or the whole chromosomal arm; and (3) multiple short LOH regions (less than about 15 Mb). Second, using the training set only, the number of LOH regions of one of these three categories was assessed for possible correlations with HDR deficiency. It was discovered that (1) the number of short LOH regions did not significantly correlate with HDR deficiency (p>0.05); (2) LOH covering an entire chromosome correlated weakly with HDR deficiency (p=0.0011); and (3) the number of large LOH regions correlated significantly with HDR deficiency (p=1.9e-8). More specifically, it was discovered that all HDR deficient tumors had a high number of large LOH regions (e.g., nine or more), while the majority of tumors likely to be HDR non-deficient had a small number of large LOH regions (FIGS. 6-8). It was probable that tumors likely to be HDR non-deficient were in fact HDR deficient due to other genetic alterations, excluding BRCA1 and BRCA2 mutations and low mRNA expression. In addition to the number of large LOH regions, the total length of these regions also correlated significantly with HDR deficiency.

These results were confirmed with the validation set: (1) the number of short LOH regions did not significantly correlate with HDR deficiency (p>0.05); (2) LOH covering an entire chromosome correlated weakly with HDR deficiency (p=0.05); and (3) the number of large LOH regions correlated significantly with HDR deficiency (p=3.9e-6).

The 134 tumors were divided from combined training and validation data sets into three groups: (1) BRCA deficient if they either had one or more deleterious mutations in BRCA1 and/or BRCA2 genes or if they had low expression of BRCA1 mRNA; (2) HDR deficient/BRCA intact if they have 9 or more large LOH regions (greater than 15 Mb but less than the length of the entire chromosome); (3) HDR intact if they have less than 9 large LOH regions (greater than 15 Mb but less than the length of the entire chromosome). Results of this analysis are presented in FIG. 9. It shows a high frequency of BRCA deficiency as well as HDR deficiency that is not due to BRCA deficiency among ovarian tumors.

Figure 10:
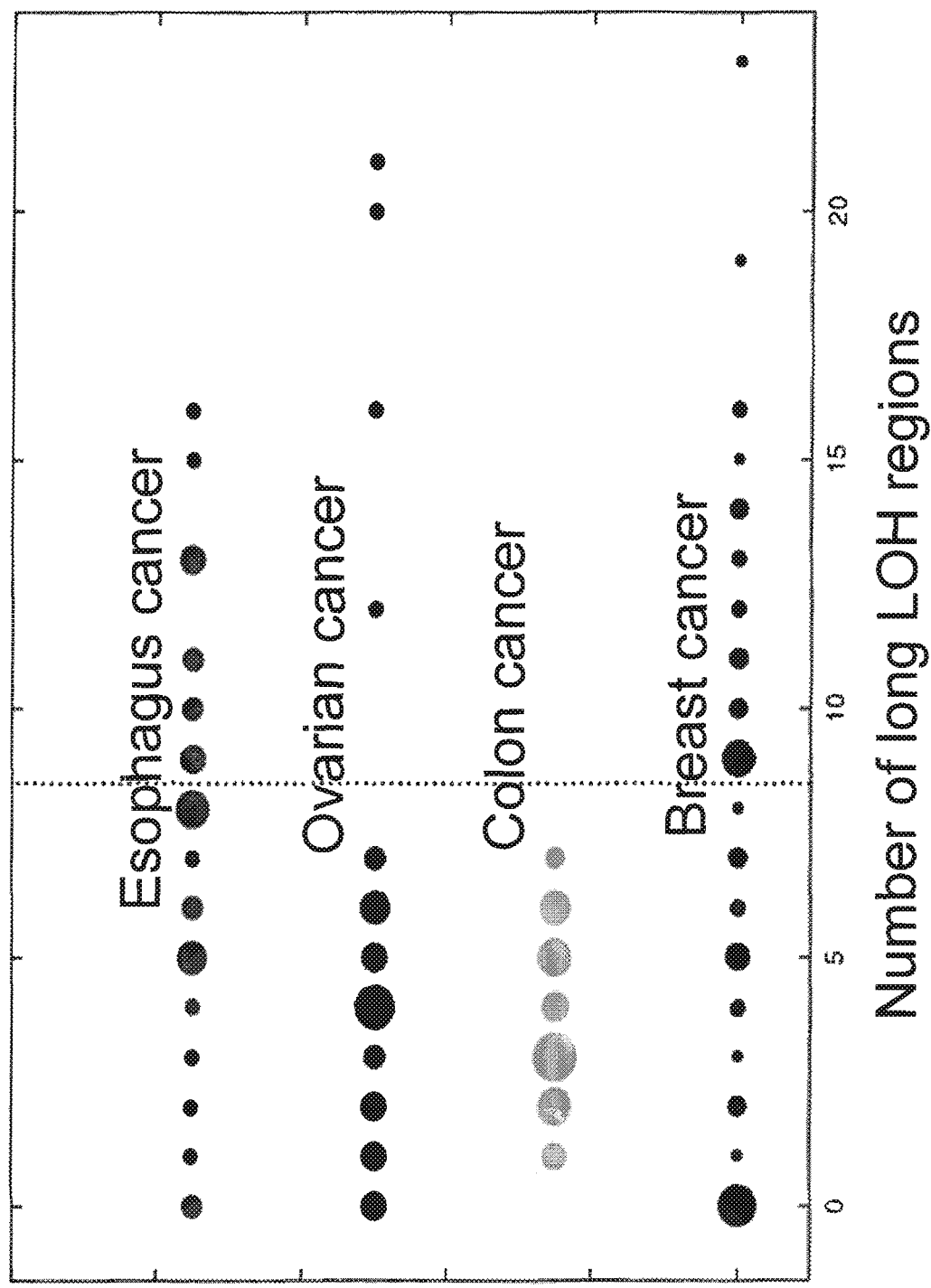
FIG. 10 is a graph plotting the number of LOH regions longer than 15 Mb and shorter than the entire chromosome for cancer cell lines for the indicated cancers. The size of the circles is proportional to the number of samples with such number of LOH regions.

FIG. 10 shows the distribution of large LOH regions (greater than 15 Mb but less than the length of the entire chromosome) for different types of cancer cell lines. The size of the circles is proportional to the number of samples with such number of large LOH regions. Frequency of HDR deficiency (cell lines with at least 9 of such large LOH regions) is the highest among breast and esophagus cancer cell lines. No HDR deficiency was observed among colon cancer cell lines. Validating the previous findings for ovarian tumors, all BRCA deficient cell lines were found to be HDR deficient as well.

Figure 11:
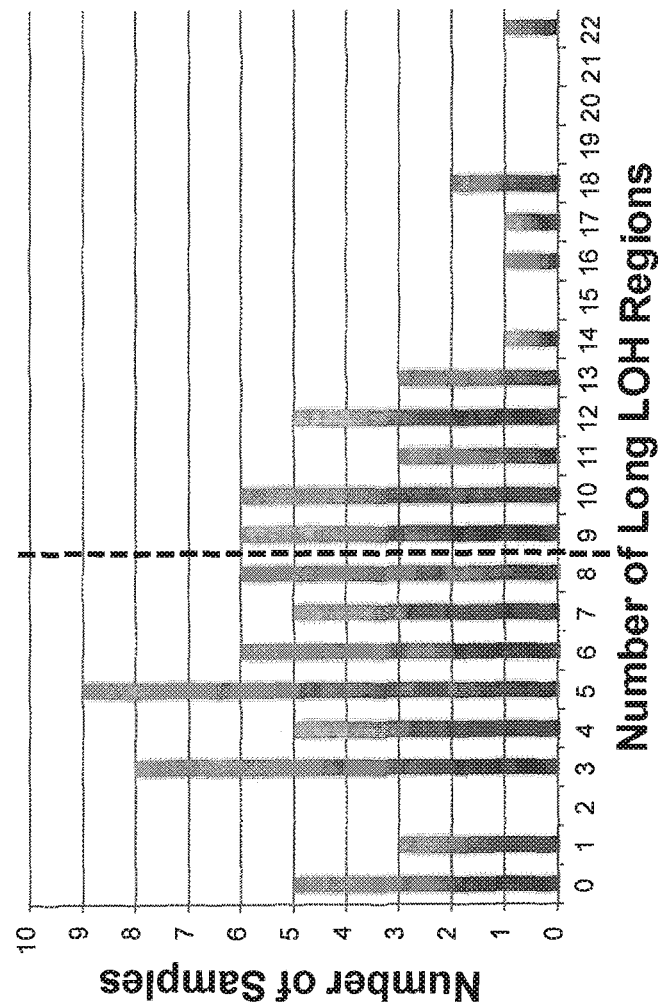
FIG. 11 is a graph plotting the number of LOH regions longer than 15 Mb and shorter than the entire chromosome for lung cancer samples.

FIG. 11 shows the distribution of large LOH regions (greater than 15 Mb but less than the length of the entire chromosome) for publicly available lung tumor data set (GSE19399 from Gene Expression Omnibus). It was observed that frequency of HDR deficiency (defined as having at least 9 large LOH regions) is quite large among lung tumors (39%).

Figure 12:
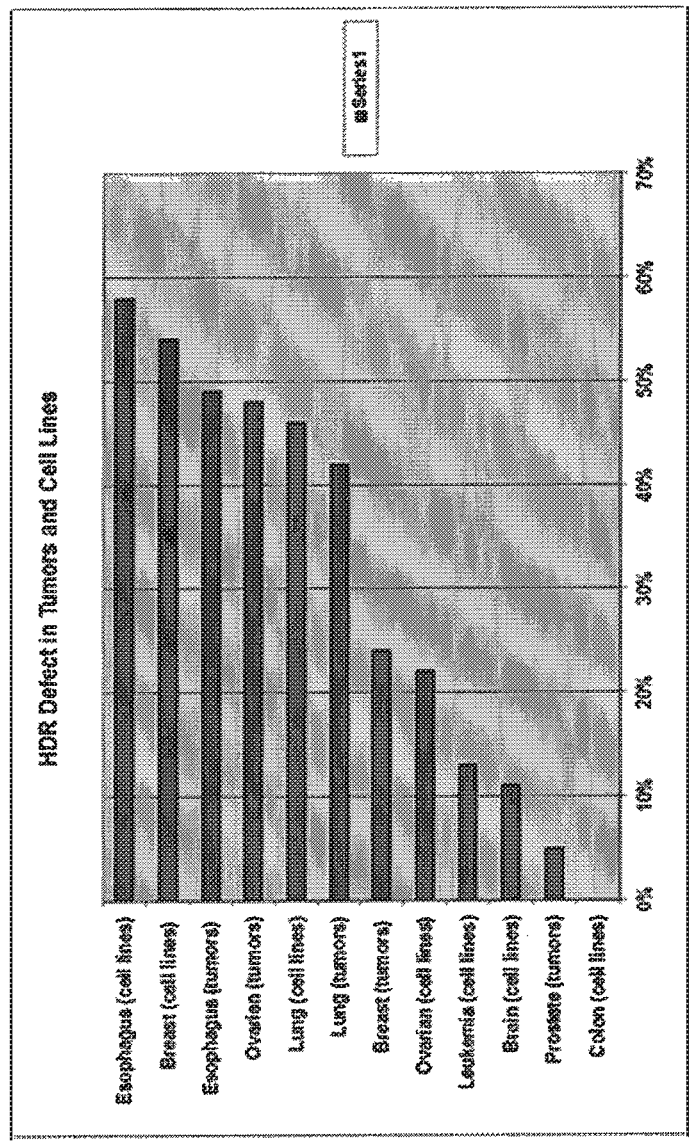
FIG. 12 is a graph plotting the percentage of the indicated cancers or cancer cell lines having an HDR deficiency.

In FIG. 12 the results of analysis of different tumors and cell lines are summarized. Frequency of HDR deficiency defined as fraction of samples with at least 9 large LOH regions (greater than 15 Mb but less than the length of the entire chromosome) is presented for several tumors and cell lines. This frequency is as high as 50% among ovarian tumors and was not observed at all among brain and colon cell lines. Thus it appears that HDR deficiency plays an important role for the majority of cancers.

Example 2—Chemo Toxicity Responses

In preparation of chemo toxicity response experiments, all cell lines were grown at 37° C. plus 5% $CO_2$ in 75 cm$^2$ tissue culture flasks (VWR International, Inc. Cat #353136) and the recommended growth medium. Before performing each experiment, each cell line was trypsinized (Invitrogen Corporation Cat #25200-056), counted, and seeded in Advanced RPMI 1640 (Invitrogen Corporation Cat #12633-020), 3% FBS, 1% penicillin/streptomycin (Invitrogen Corporation Cat #15140-122) at 2500 cells or 5000 cells in 100 μL media per well from columns 2-12 of 96-well polystyrene microplates with clear bottom (Perkin Elmer Cat #6005181), leaving column 1 with 100 μL per well of media only. The cell-seeded plates were then incubated at 37° C. plus 5% $CO_2$ overnight.

Two different final drug concentration working stocks were prepared. In cases where 100% DMSO was required for drug solubility, Advanced RPMI 1640 was used as the diluent for the highest concentration. Advanced RPMI 1640 plus a predetermined amount of DMSO equal to the total DMSO in the high concentration working stock was used for the low concentration, with a maximum of 60% DMSO used for the lowest concentration. This was done to keep the DMSO concentrations equal in every well and prevent non-specific cell death as a result of DMSO. The lower of the two drug concentrations was placed in a 96-well, thin-wall PCR cycle plate (Robbins Scientific Cat #1055-00-0) in rows A-D, column 12, while the higher concentration was placed in rows E-H, column 12, of the same plate. Serial dilutions of 1:2 or 1:3 were performed in a descending manner from column 12 to 3, leaving columns 1 and 2 to be used for no cell/no drug and no drug controls. This allowed for quadruplet data points for each drug concentration. Once dilutions were complete, 5 μL was transferred from the dilution plate to the corresponding well of the seeded cell plate. Plates receiving drugs were then incubated at 37° C. plus 5% $CO_2$ for either 3 days or 6 days.

Following a 3-day or 6-day dose regimen, ATPlite assays (Perkin Elmer cat #6016941) were run on each well of each plate according to the ATPLite Assay protocol. The luminescence was then read on a FUSION machine and saved as a .CSV file. For each cell-line and drug combination, the four replicates of the no-drug control were averaged and divided by 100 to create a "normalization factor" used to calculate a normalized percent survival. The normalized percent survival for the no-drug controls was 100%. The four replicates of the cell-plus-drug wells were averaged and divided by the normalization factor for each drug concentration. The percent survival for each drug concentration, starting with a concentration equal to 0, was used to calculate an $IC_{50}$ using proprietary software.

Figure 13:
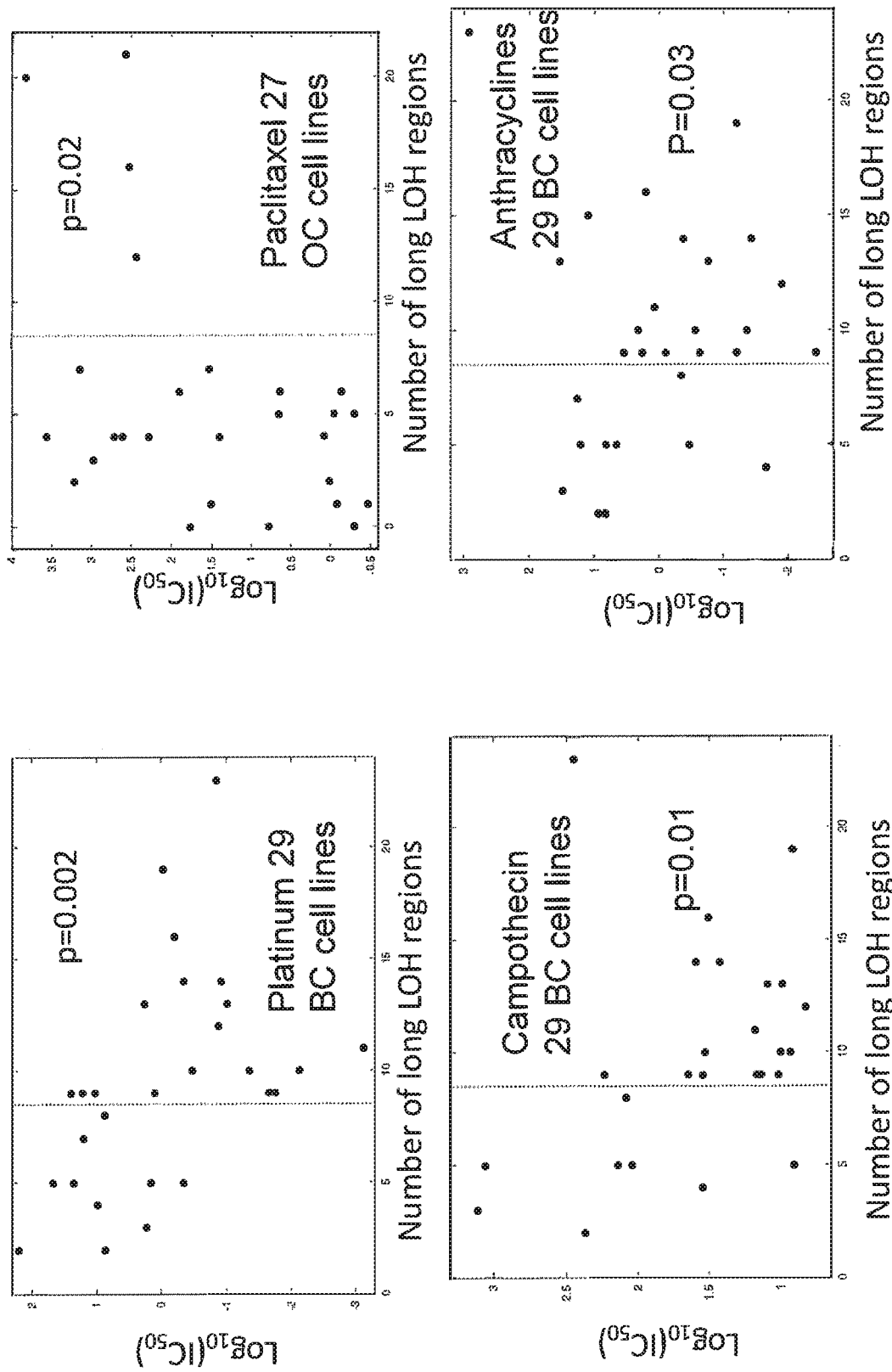
FIG. 13 contains graphs plotting the $IC_{50}$ values ($Log_{10}$ ($IC_{50}$) of camptothecin, as well as averaged $Log_{10}(IC_{50})$ values for platinum compounds (oxaliplatin, cisplatin, and carboplatin), or anthracyclines (doxorubicin and epirubicin) when exposed to 29 breast cancer cell lines having the indicated number of LOH regions longer than 15 Mb and shorter than the entire chromosome or the $IC_{50}$ values ($Log_{10}(IC_{50})$) of paclitaxel when exposed to 27 ovarian cancer cell lines having the indicated number of LOH regions longer than 15 Mb and shorter than the entire chromosome. The dashed lines place a threshold number at nine.

FIG. 13 shows response to chemotherapy for breast and ovarian cancer cell lines. On y-axis are indicated values of $Log_{10}(IC_{50})$ for different chemotherapy drugs (camptothecin, as well as averaged results for platinum compounds (oxaliplatin, cisplatin, and carboplatin) or anthracyclines (doxorubicin and epirubicin)) when exposed to 29 breast cancer cell lines as well as $Log_{10}(IC_{50})$ of paclitaxel when exposed to 27 ovarian cancer cell lines. On the x-axis the number of large LOH regions longer than 15 Mb and shorter than the entire chromosome are indicated for these cell lines. The dashed lines place a threshold number at nine.

Figure 14:
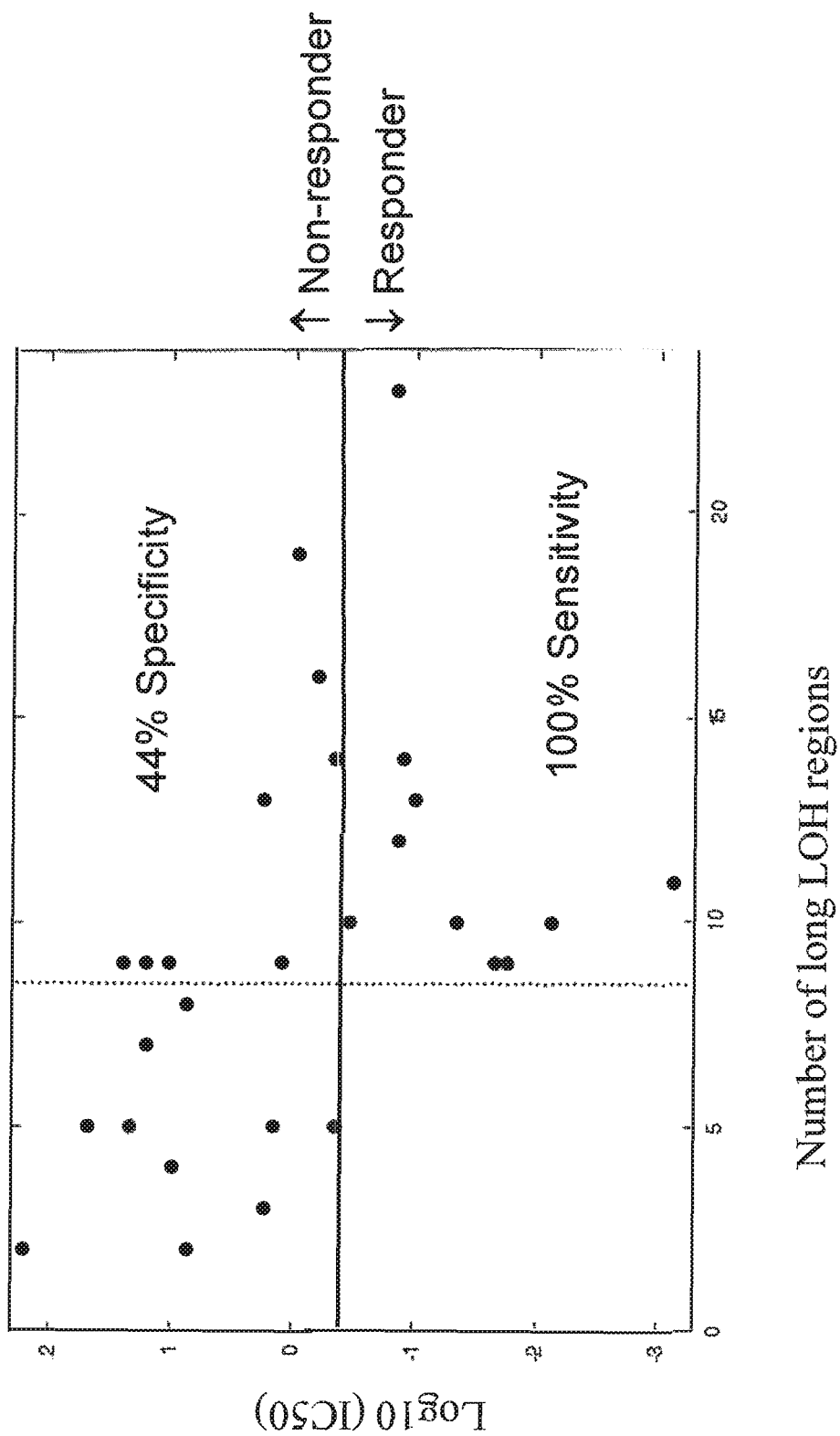
FIG. 14 is a labeled version of a graph from FIG. 13 that plots the averaged $Log_{10}(IC_{50})$ values of platinum compounds (oxaliplatin, cisplatin, and carboplatin) when exposed to 29 breast cancer cell lines having the indicated number of LOH regions longer than 15 Mb and shorter than the entire chromosome.

FIG. 14 is a version of a graph from FIG. 13 that indicates specificity and sensitivity among responders and non-responders to treatment with platinum compounds (oxaliplatin, cisplatin, and carboplatin) when exposed to 29 breast cancer cell lines. The dashed lines place a threshold number of large LOH regions longer than 15 Mb and shorter than the entire chromosome at nine. The solid line divides cell lines into responders and non-responders.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating cancer, comprising:
   predicting a cancer patient's response to a cancer treatment regimen comprising a DNA damaging agent, an anthracycline, a topoisomerase I inhibitor, radiation, and/or a PARP inhibitor, wherein predicting the cancer patient's response to the cancer treatment regimen comprises:
   determining, in genomic DNA derived from a cancer cell obtained from the patient, the total number of LOH regions in at least one pair of human chromosomes of said DNA that are longer than a first length but shorter than the length of the whole chromosome containing the LOH region, wherein said at least one pair of human chromosomes is not a human X/Y sex chromosome pair, wherein said first length is about 1.5 or more megabases and wherein the cancer cell is selected from the group consisting of breast cancer cells, ovarian cancer cells, leukemia cancer cells, esophageal cancer cells, lung cancer cells, and prostate cancer cells;
   correlating said total number of LOH regions that is greater than a reference number that is at least 6 with an increased likelihood that said cancer patient will respond to said cancer treatment regimen; and
   based on the correlating of said total number of LOH regions with an increased likelihood that said cancer patient will respond to said cancer treatment regimen, administering to the cancer patient a treatment regimen comprising a DNA damaging agent, an anthracycline, a topoisomerase I inhibitor, radiation, and/or a PARP inhibitor.

2. The method of claim 1, wherein said LOH regions are determined in at least ten pairs of human chromosomes.

3. The method of claim 1, wherein said total number of LOH regions.

4. The method of claim 1, wherein said first length is about 6 or more megabases.

5. The method of claim 1, wherein said reference number is at least 8.

6. The method of claim 1, wherein said at least one pair of human chromosomes is not human chromosome 17.

7. The method of claim 1, wherein said DNA damaging agent is cisplatin, carboplatin, oxalaplatin, or picoplatin, said anthracycline is epirubicin or doxorubicin, said topoisomerase I inhibitor is campothecin, topotecan, or irinotecan, or said PARP inhibitor is iniparib, olaparib or veliparib.

8. A method of treating cancer, comprising:
   predicting a cancer patient's response to a treatment regimen including paclitaxel or docetaxel, wherein predicting the cancer patient's response to a treatment regimen comprises:
   determining, in genomic DNA derived from a cancer cell obtained from the patient, the total number of LOH regions in at least one pair of human chromosomes of said DNA that are longer than a first length but shorter than the length of the whole chromosome containing the LOH region, wherein said at least one pair of human chromosomes is not a human X/Y sex chromosome pair, wherein said first length is about 1.5 or more megabases, wherein the cancer cell is selected from the group consisting of breast cancer cells, ovarian cancer cells, leukemia cancer cells, esophageal cancer cells, lung cancer cells, and prostate cancer cells;
   correlating said total number of LOH regions that is greater than a reference number that is at least 6 with an increased likelihood that said cancer patient will not respond to a treatment regimen including paclitaxel or docetaxel; and
   based on the correlating of said total number of LOH regions with an increased likelihood that said cancer patient will respond to said cancer treatment regimen, administering to the patient a treatment regimen including a DNA damaging agent, an anthracycline, a topoisomerase I inhibitor, radiation, and/or a PARP inhibitor.

9. The method of claim 8, wherein said LOH regions are determined in at least ten pairs of human chromosomes.

10. The method of claim 8, wherein said total number of LOH regions is 9 or more.

11. The method of claim 8, wherein said first length is 6 or more megabases.

12. The method of claim 8, wherein said reference number is at least 8.

13. The method of claim 8, wherein said at least one pair of human chromosomes is not human chromosome 17.

* * * * *

UNITED STATES PATENT AND TRADEMARK OFFICE
CERTIFICATE OF CORRECTION

PATENT NO. : 10,851,425 B2  
APPLICATION NO. : 16/576643  
DATED : December 1, 2020  
INVENTOR(S) : Victor Abkevich et al.

Page 1 of 1

It is certified that error appears in the above-identified patent and that said Letters Patent is hereby corrected as shown below:

In the Claims

Claim 8, Column 34, Line 29, should be corrected to read "patient will not respond to said cancer regimen,"

Signed and Sealed this  
Fifteenth Day of June, 2021

Drew Hirshfeld  
*Performing the Functions and Duties of the*  
*Under Secretary of Commerce for Intellectual Property and*  
*Director of the United States Patent and Trademark Office*